(12) United States Patent
Mueller et al.

(10) Patent No.: US 9,988,685 B2
(45) Date of Patent: Jun. 5, 2018

(54) METHODS AND KITS FOR DIAGNOSING, PROGNOSTICATING RISK/OUTCOME, AND/OR TREATING BREAST CANCER

(71) Applicant: Queen's University at Kingston, Kingston (CA)

(72) Inventors: Christopher Robert Mueller, Kingston (CA); Kirsten A. Nesset, Kingston (CA)

(73) Assignee: QUEEN'S UNIVERSITY AT KINGSTON, Kingston, Ontario (CA)

( * ) Notice: Subject to any disclaimer, the term of this patent is extended or adjusted under 35 U.S.C. 154(b) by 166 days.

(21) Appl. No.: 14/203,818

(22) Filed: Mar. 11, 2014

(65) Prior Publication Data

US 2014/0272957 A1 Sep. 18, 2014

Related U.S. Application Data

(60) Provisional application No. 61/793,326, filed on Mar. 15, 2013.

(51) Int. Cl.
*C07H 21/04* (2006.01)
*C12Q 1/68* (2018.01)

(52) U.S. Cl.
CPC ..... *C12Q 1/6886* (2013.01); *C12Q 2600/154* (2013.01)

(58) Field of Classification Search
None
See application file for complete search history.

(56) References Cited

U.S. PATENT DOCUMENTS

2010/0172880 A1* 7/2010 Laird ............... C12Q 1/6886 424/93.7

OTHER PUBLICATIONS

Lien et al. (J. of Pathology, vol. 209, pp. 317-327, Apr. 25, 2006).*
Kirsten Anne Nesset (Characterization of Glucocoricoid receptor promoter methylation in breast cancer, Thesis submitted to Queen's University, Canada, Sep. 2012).*
Fackler et al. Cancer Research, vol. 71, No. 19, pp. 6195-6207, Oct. 2011.*
Lustberg (Curr Breast Cancer Rep, vol. 3, No. 1, pp. 24-43, Mar. 2011).*
Connolly et al. (J. Mammary Gland Biol. Neoplasia, vol. 17, pp. 191-204, 2012).*
Faryna et al. (FASEB J. vol. 26, pp. 4937-4950, 2012).*
Fackler et al. (Cancer Research, vol. 71, No. 19, pp. 6195-6207, Oct. 2011).*
Birgisdottir et al. "Epigenetic Silencing and Deletion of the BRCA1 Gene in Sporadic Breast Cancer" Breast Cancer Research 2006 8:R38.
Breslin et al. "Multiple Promoters Exist in the Human GR Gene, One of Which Is Activated by Glucocorticoids" Molecular Endocrinology 2001 15(8):1381-1395.
Buxant et al. "Estrogen Receptor, Progesterone Receptor, and Glucocorticoid Receptor Expression in Normal Breast Tissue, Breast In Situ Carcinoma, and Invasive Breast Cancer" Applied Immunohistochemistry & Molecular Morphology 2010 18(3):254-257.
Cao-Lei et al. "Transcriptional Control of the Human Glucocorticoid Receptor: Identification and Analysis of Alternative Promoter Regions" Human Genetics 2011 129:533-543.
Kang et al. "DNA Methylation Profiles of Gastric Carcinoma Characterized by Quantitative DNA Methylation Analysis" Laboratory Investigation 2008 88:161-170.
Kay et al. "Loss of Glucocorticoid Receptor Expression by DNA Methylation Prevents Glucocorticoid Induced Apoptosis in Human Small Cell Lung Cancer Cells" PLoS ONE 2011 6(10):e24839.
Lien et al. "Differential Expression of Glucocorticoid Receptor in Human Breast Tissues and Related Neoplasms" Journal of Pathology 2006 209:317-327.
Lind et al. "ADAMTS1, CRABP1, and NR3C1 Identified as Epigenetically Deregulated Genes in Colorectal Tumorigenesis" Cellular Oncology 2006 28:259-272.
Ritter et al. "The Unliganded Glucocorticoid Receptor Positively Regulates the Tumor Suppressor Gene BRCA1 through GABP Beta" Molecular Cancer Research 2012 10:558-569.
Turner et al. "Highly Individual Methylation Patterns of Alternative Glucocorticoid Receptor Promoters Suggest Individualized Epigenetic Regulatory Mechanisms" Nucleic Acids Research 2008 36(22):7207-7218.
Turner, J.D. and Muller, C.P. "Structure of the Glucocorticoid Receptor (NR3C1) Gene 5' Untranslated Region: Identification, and Tissue Distribution of Multiple New Human Exon 1" Journal of Molecular Endocrinology 2005 35:283-292.
Turner et al. "Transcriptional Control of the Glucocorticoid Receptor: CpG Islands, Epigenetics and More" Biochemical Pharmacology 2010 80:1860-1868.
Wu et al. "DNA Methylation Profiling of Ovarian Carcinomas and Their In Vitro Models Identifies HOXA9, HOXB5, SCGB3AI, and CRABPI as Novel Targets" Molecular Cancer 2007 6:45.

\* cited by examiner

*Primary Examiner* — Jeanine A Goldberg
(74) *Attorney, Agent, or Firm* — Licata & Tyrrell P.C.

(57) ABSTRACT

Methods and kits for diagnosing, prognosticating risk of, and selecting and/or administering a therapy for breast cancer based upon detection of methylated glucocorticoid receptor gene or measurement of glucocorticoid receptor and BRCA1 gene expression levels are provided.

6 Claims, 11 Drawing Sheets

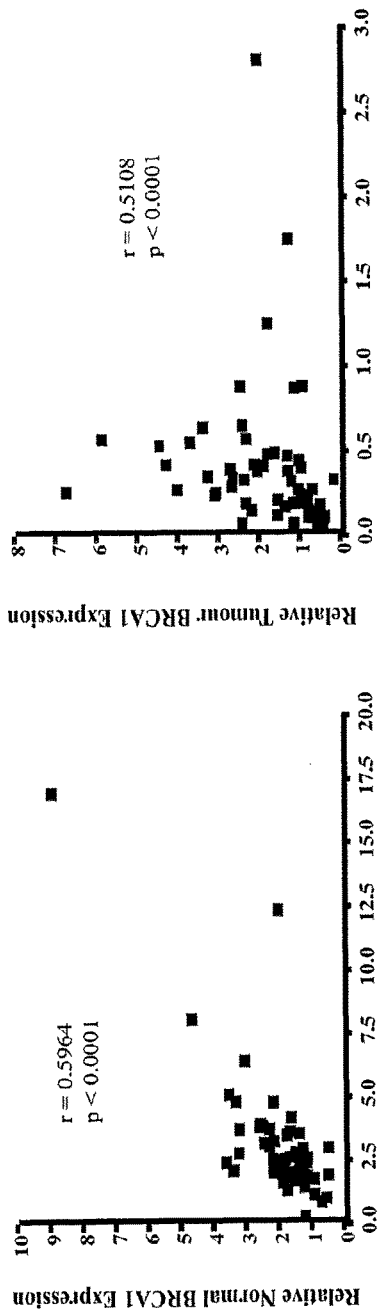
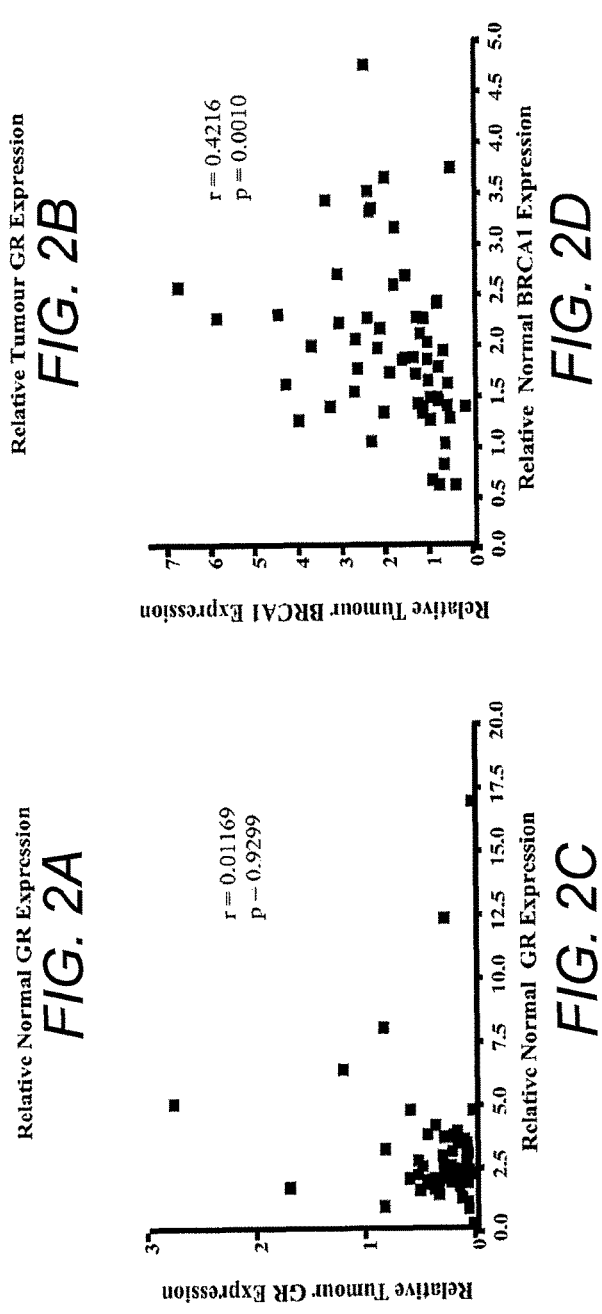

```
   1 gagcaggatt aggtggagct gcggcagccc ccgcccgtgt caggagctgg caagcgatgt
  61 cacctgtggg ggcgcaaaag ttacctcccc aaaccctaaa cccacacagc acaacctttc
 121 ccagagtcac aaaaatcata atctgtgccg cacaaggtag gaggctcggt cccggcatcg
 181 tccaagcctt cccgacgcgg cgagctgggg aagggagctg gggcgggggc ttcccgcacg
 241 ggcacccctc gccccacggc cctctccttt ctcaggacgg accacgagtt cccttcccct
 301 tggactgagg gggaagctcc taacaggaac atctgtaggg agttgaacgc tggcatttta
 361 aagctgcctg tattttgttt tatttgtagg ggcaggggtc ctatgaacgt gatagggtga
 421 gcaacgcaca gagtcgaggg cagcaaatgt caagattcgg gggtggggcc tgcaccggga
 481 acttggacgc gggccctggc cggggtggaa gaagaggtca ggagtttcgg aaggggggct
 541 atatttcgcc agcaacttac tatttcgcct gcaacttgct tttaagcctg ccgcccctg
 601 ctttccttaa tcataataat aaaaaaaaag tgcaaagaaa tccagctcgc tggaggtttt
 661 gcatttggcg tgcaacttcc ttcgagtgtg agcacattgg gcgggagggg tggggttga
 721 acttggcagg cggcgcctcc ttctgccgcc gccgccgcct cgcagactcg gggaagaggg
 781 tgggggacgg tcggggcgcg ggggagggtg ggttctgctt tgcaacttct ctcccagtgc
 841 gagagcgcgg cggcggcagc tgaagacccg gccgcccaga tgatgcggtg gtgggggacc
 901 tgccggcacg cgactccccc ccgggcccaa agtacgtatg cgccgaccccc cgctatcccg
 961 tcccttccct gaagcctccc cagagggcgt gtcaggccgc ccggccccga gcgcggccga
1021 gacgctgcgg caccgtttcc gtgcaacccc gtagccccttt tcgaagtgac acacttcacg
1081 caactcggcc cggcggcggc ggcgcgggcc actcacgcag ctcagccgcg ggaggcgccc
1141 cggctcttgt ggcccgcccg ctgtcacccg caggggcact ggcggcgctt gccgccaagg
1201 ggcagagcga gctcccgagt gggtctggag ccgcggagct gggcggggc gggaaggagg
1261 tagcgagaaa agaaactgga gaaactcggt ggccctctta acgccgcccc agagagacca
1321 ggtcggcccc cgccgctgcc gccgccaccc ttttcctgg ggagttgggg gcggggggcg
1381 aagcgcggcg caccgggcgg ggcggccacg ccaggggacg cgggcgtgca ggcgccgtcg
1441 gggccggggt ggcggggccc cgcgcgaggg cgtgggggca gggaccgcgg gcgcccctgc
1501 agttgccaag cgtcaccaac aggttgcatc gttccccgcg gccgccgcgc ggcccctcgg
1561 gcggggagcg gccgggggtg gagtgggagc gcgtgtgtgc gagtgtgtgc gcgccgtggc
1621 gccgcctcca cccgctcccc gctcggtccc gctcgctcgc ccaggccggg ctgcccttc
1681 gcgtgtccgc gctctcttcc ctccgccgcc gcctcctcca ttttgcgagc tcgtgtctgt
1741 gacgggagcc cgagtcaccg cctgcccgtc ggggacggat tctgtgggtg gaaggagacg
1801 ccgcagccgg agcggccgaa gcagctggga ccgggacggg gcacgcgcgc ccggaagccc
1861 cgacccgcgg agcccggcgc ggggcggagg gctggcttgt cagctgggca atgggagact
1921 ttcttaaata ggggctctcc ccccacccat ggagaaaggg gcggctgttt acttccttt
1981 tttagaaaaa aaaaatatat ttccctcctg ctccttctgc gttcacaagc taagttgttt
2041 atctcggctg cggcgggaac tgcggacggt ggcgggcgag cggctcctct gccagaggta
2101 agaagcgagg cgggaggggg ccggggcgcg ctcgctcccc cgaggtgccg ctgggaccgg
2161 agacaactcg ggggccgccg cggagcccta caaactttta ttagcctcgg ggagtggggg
2221 tgggggggctg gcaagggccg ggcgacggtg acgaaaggc agcgcgcggg tgacagcgct
2281 ggcctcttcc tctccctccg ccggcgtccc ctggccgggc cgaggggag gaacctgacc
2341 tcggacggcg agcggagccc tgtcgaactg ccggggggctt cgagcctctc attcctcgcg
2401 ggaatcctgg cctcttttct cccctagtg tcccctttcc ctccaagggg gtcgcccgac
2461 acccgttttc gtggtgaacg ctaagccgcg tctgaatttt actcgcccga atatttgcac
2521 gccacccgg cgcgcccgag cgcgagcccg ggctccgggg aggccccggc ggcgcctggc
2581 ttgaggaggg cgtgcgggc gcgtgagggt gcacacgcgg ggggctgaca gcccgcaact
2641 tggagactgc ggccggggcc ggcgttatct gttagaagtg ggcgtgtcgg agagagaact
2701 caacaggtct ggacgtactt ctcttttaac ctcgcacttt tttctcttct ccaccccgc
2761 cccgcaaggg cttgctcttt agcgtttgtt gttaattcgc gctgaggtt tctaagtggc
2821 cccttttaga aaaagacccc ctgtaaccgt aatggttttg tgctgcgatt tttacaagtg
2881 ctagtttgac gtttggggtt gcagacttga taattgcaac cttgtaatac cacttaagac
2941 cctctggcat ggttcattag ggccaattaa tgtggctggg ttatttgcaa cttaaactgg
3001 gggataatgt cgcttgaggg agcgttttcg ttttaggaaa tattgttttg gtttcgggtt
3061 tgaaggcagc tgtcaaaaaa gcggcatgga aattcattgg gctccattcg atacctcgtg
3121 tttagagatc gttatcgcct cagataaacg gggcagagag gtggggagat aagcagttta
3181 ccctcaagat ttgtagtggc aagtccacac ccctctctct accttcatat tcacttttca
```

*FIG. 9A*

```
3241 gtgagggcca gtgacattta tgctgcctaa cgtcatcgca taggaaaagt tacctttat
3301 tggacgggat ttgactatag tgtcccaaat gcgcttctcc gtcttagccc atctcttaaa
3361 acaccctgat taacgatata ctaacagtct tactctcttg agaataggct gagaattggg
3421 ataggtgaag gtttggatag gtgaaggcag agaaaattat tttgaacatt ttactggata
3481 cagttgtacc tgaatttata tgaatgtgat tttacggttc tgtgttttc cattttcag
3541 tacttcgata tttgtttgga aaggaaagaa cttagagatg taatagcatt tcatattgag
3601 gatctcaagc aatgtaaaca aatgtagctt aatctagatg tttttgtgag ttatgataag
3661 ggtcagctat atttaagtta tgtaagctaa caacgtagtg agaaactact acaccttctc
3721 ttctgctctt taaaatctaa attttagttg gcctatataa agtgtatctc attcatata
3781 tccaaaattt ggaggtaggc acatccagtc agaagtatgg gttaaaaagc cttttcccag
3841 cctgtcggaa gataagcaga tcagcattgt ttatttttca aagaaaacgt gcatggttca
3901 ccagttggtt gtactcaaag gtttggatgt gtgactagct ggtaggaggg aaatttggaa
3961 gtaattaggg attgagaatt ctagcatagt atttatcaaa tgttatatgt attggttctc
4021 agaaaagcaa acagccgtga ttgaaaagag gtaggaattt taatgatcac acttccttt
4081 tttgaaatta aatactttga catcaacttg aaccttcaga ataatcagat gtaatgaatt
4141 ataatgtctg tgattaacaa agctacacgt tcagtaatcg gcaggatgaa tagccaagct
4201 tagttcgata cacttttgcc ctcagctgtg caaatggatt gcattgtact tttaaatgtg
4261 gcatgctgaa tgggagcagg ggacatggct ttttattctg gaagatagaa actactcttc
4321 tggtaacaaa gaatttgatt cggagttaac taaaaggttc atttaacaag ctgcctctta
4381 ctaatcggat caggaagata atgtgacttt agagcttatg atgttttccc ccgttttg
4441 ttttttgttt tgtagttgat attcactgat (SEQ ID NO:1)
```

METHODS AND KITS FOR DIAGNOSING, PROGNOSTICATING RISK/OUTCOME, AND/OR TREATING BREAST CANCER

This patent application claims the benefit of priority from U.S. Provisional Application Ser. No. 61/793,326, filed Mar. 15, 2013, the content of which is hereby incorporated by reference in its entirety.

FIELD OF THE INVENTION

The present invention provides methods and kits for diagnosing, prognosticating risk and/or outcome of, and selecting and/or administering a therapy for breast cancer based upon detection of a methylated glucocorticoid receptor gene and/or measurement of glucocorticoid receptor gene expression levels.

BACKGROUND OF THE INVENTION

The glucocorticoid receptor (GR) is a steroid hormone receptor that serves as a transcriptional regulator in the human stress response when bound to its ligand, cortisol. A study of gastric carcinomas found that the GR promoter was methylated in 20-30% of cases, which was three times higher than in normal gastric tissue (Kang, et al. (2008) *Laboratory Investigation; a Journal of Technical Methods and Pathology* 88:161-70). Small cell lung carcinoma (SCLC) cell lines also exhibited increased promoter methylation (Kay, et al. (2011) *PloS One* 6:e24839). In addition, the GR gene was methylated in 25% of colorectal carcinomas and 35% of colorectal cancer cell lines, and methylation was associated with a decrease in gene expression (Lind, et al. (2006) *Cell. Oncol.* 28:259-272). However, methylated GR gene was not detected in ovarian cancer (Wu, et al. (2007) *Mol. Cancer* 6:45).

In breast cancer, GR protein expression has been disclosed to decrease significantly with tumor histologic grade, with one study reporting expression reduced below 50% that of normal tissue (Lien, et al. (2006) *J. Pathol.* 209:317-27). Investigation of estrogen receptor (ER)-negative and progesterone receptor (PR)-negative tissues has also shown that all were negative for GR, suggesting that GR loss may occur early during breast tumorigenesis (Buxant, et al. (2010) *Appl. Immunohist. Mol. Morph.* 18:254-7).

The human GR gene (NR3C1) spans 80 kbp on chromosome 5 and contains 8 coding exons (2-9) and nine tissue-specific alternative first exons (Turner, et al. (2005) *J. Mol. Endocrinol.* 35:283-92) located in two distinct promoter regions: the distal promoter approximately 30 kbp upstream of the translation start site and the proximal promoter located in a 3 kbp CpG island 5 kbp upstream from the ATG start codon (Turner, et al. (2010) *Biochem. Pharmacol.* 80:1860-8; Breslin, et al. (2001) *Mol. Endocrinol.* 15:1381-95). Cloning of the intronic regions between the alternative first exons into luciferase reporters has shown that each alternative first exon has its own unique promoter, and methylation of these promoters by SssI methyltransferase successfully reduced activity to below 10%, indicating that individual first exon promoters are susceptible to epigenetic control (Cao-Lei, et al. (2011) *Human Genet.* 129:533-43). It has also been suggested that methylation of these promoters may be subject to individualized, highly variable regulation (Turner, et al. (2008) *Nucl. Acids Res.* 36:7207-18). A previous study investigating GR promoter methylation in breast cancer disclosed no detectable methylation (Lien, et al. (2006) supra).

A role for unliganded GR as a positive regulator of BRCA1 activity has been disclosed (Ritter, et al. (2012) *Mol. Cancer Res.* 10(4):558-69). BRCA1 is an important gene in breast cancer etiology as its protein product is involved in cell regulatory processes including DNA repair (Birgisdottir, et al. (2006) *Breast Cancer Res.* 8:R38).

SUMMARY OF THE INVENTION

An aspect of the present invention relates to a method for diagnosing breast cancer in a subject by detecting a methylated glucocorticoid receptor promoter in the subject wherein detection of the methylated glucocorticoid receptor promoter is indicative of breast cancer in the subject. In one embodiment, detection of the methylated glucocorticoid receptor promoter is performed in a breast tissue sample obtained from the subject. In another embodiment, detection of the methylated glucocorticoid receptor promoter is performed in a blood, nipple aspirate, ductal lavage, serum or plasma sample obtained from the subject. In some embodiments, this is performed in a cell-free system.

Another aspect of the present invention relates to a method for diagnosing breast cancer in a subject by obtaining a sample from the subject; and detecting any methylated glucocorticoid receptor promoter in the sample; wherein detection of methylated glucocorticoid receptor promoter in the sample is indicative of breast cancer in the subject. In one embodiment, the sample obtained from the subject is a breast tissue sample. In another embodiment, the sample obtained from the subject is a blood, nipple aspirate, ductal lavage, serum or plasma sample. In one embodiment, the methylated glucocorticoid receptor promoter is detected in DNA isolated from the sample.

Another aspect of the present invention relates to a method for diagnosing breast cancer in a subject comprising measuring a level of glucocorticoid receptor gene expression in the subject; measuring a level of BRCA1 gene expression in the subject; and comparing measured levels of glucocorticoid receptor and BRCA1 gene expression in the subject with respective standard levels of glucocorticoid receptor and BRCA1 gene expression; wherein a low level of glucocorticoid receptor gene expression as compared to the standard level and an abnormal level of BRCA1 gene expression in the subject as compared to the standard level is indicative of breast cancer. In one embodiment, the levels of glucocorticoid receptor and BRCA1 gene expression are measured in a breast tissue sample, a ductal lavage sample or a nipple aspirate sample obtained from the subject. In another embodiment, the levels of glucocorticoid receptor and BRCA1 gene expression are measured in a blood, nipple aspirate, ductal lavage, serum or plasma sample obtained from the subject. In one embodiment, an RNA level of glucocorticoid receptor and/or BRCA1 gene expression is measured. In another embodiment, a protein level of glucocorticoid receptor and/or BRCA1 gene expression is measured.

Another aspect of the present invention relates to a method for diagnosing breast cancer in a subject by obtaining a sample from the subject; measuring a level of glucocorticoid receptor gene expression in the subject; measuring a level of BRCA1 gene expression in the subject; and comparing measured levels of glucocorticoid receptor and BRCA1 gene expression in the subject with respective standard levels of glucocorticoid receptor and BRCA1 gene expression; wherein a low level of glucocorticoid receptor gene expression as compared to the standard level and an abnormal level of BRCA1 gene expression in the subject as compared to the standard level is indicative of breast cancer. In one embodiment, a breast tissue sample, a ductal lavage sample or a nipple aspirate sample is obtained from the subject. In one embodiment, an RNA level of glucocorticoid receptor and/or BRCA1 gene expression is measured. In another embodiment, a protein level of glucocorticoid receptor and/or BRCA1 gene expression is measured.

Another aspect of the present invention relates to a method for prognosticating risk and/or outcome of a subject diagnosed with breast cancer. In this method, methylated glucocorticoid receptor promoter indicative of the outcome of the subject is detected. This aspect of the present invention may further comprise selecting and/or administering a treatment for breast cancer based upon the prognosticated outcome and/or risk. In one embodiment of this method, detection of the methylated glucocorticoid receptor promoter is performed in a breast tissue sample, ductal lavage sample or needle aspirate sample obtained from the subject. In another embodiment, detection of the methylated glucocorticoid receptor promoter is performed in a blood, serum or plasma sample obtained from the subject. In one embodiment, the method may further comprise the step of measuring a level of BRCA1 gene expression in the subject and comparing the measured level to a standard level. In one embodiment, the method may further comprise determining whether the breast cancer is ER+ or ER−, wherein this determination relates to selecting and/or administering therapy.

Yet another aspect of the present invention relates to a kit for diagnosing breast cancer and/or prognosticating outcome of a subject with breast cancer. The kit comprises means for measuring a methylated glucocorticoid receptor promoter in a sample from a subject, and optionally means for measuring a level of BRCA1 gene expression in a sample from a subject and/or means for determining whether the breast cancer is ER+ or ER−.

BRIEF DESCRIPTION OF THE FIGURES

FIGS. 2A through 2D show correlative analysis of gene expression in normal and tumor tissue. Relative gene expression between matched normal and tumor samples from 59 patients were obtained by normalizing quantitative reverse transcriptase polymerase chain reaction (qRT-PCR) gene expression data in normal and tumor tissue for each sample to gene expression levels in A00235 normal tissue. FIG. 2A shows GR and BRCA1 expression in normal tissue. Gene expression is significantly correlated in normal tissue samples analyzed with Spearman correlation coefficient r=0.60 (p<0.0001). FIG. 2B shows GR and BRCA1 expression in tumor tissue. Gene expression is significantly correlated in tumor tissue samples analyzed with r=0.51 (p<0.0001). FIG. 2C shows GR expression in normal and tumor tissue. GR expression is not associated between normal and tumor tissue with r=0.01169 (p=0.9299). FIG. 2D shows BRCA1 expression in normal and tumor tissue. BRCA1 expression was weakly correlated between normal and tumor tissue with r=0.42 (p=0.001).

FIG. 3A shows that GR expression was decreased in all tumor samples, excluding sample D01394 (fold response=1.07) with an average decrease in GR expression of 13.81-fold (standard deviation=15.78). Sample D02144 had no GR expression in tumor tissue (calculated as an infinite fold decrease in expression). Therefore, this sample was not included in the average fold response calculations, or on the graph. FIG. 3B shows that BRCA1 expression from normal to tumor tissue was generally smaller and more variable with both increases and decreases observed. For tumors with increased BRCA1 expression (21 samples), the average was 1.79-fold (standard deviation=0.67). The remaining tumors (38 samples) had an average decrease of 2.22-fold (standard deviation=2.48).

FIG. 7A shows that tumors methylated at the prox GR 5 promoter region (A01719, B02275, D01354, D02291, D02551) had significantly lower relative GR expression compared to unmethylated tumors ($p=4.88 \times 10^{-6}$). In contrast, FIG. 7B shows that there was no significant difference in BRCA1 expression between prox GR 5 methylated or unmethylated tumors ($p=0.52$).

FIGS. 9A and 9B show the promoter sequence and 5' untranslated region of the human GR gene (SEQ ID NO:1).

DETAILED DESCRIPTION OF THE INVENTION

It has now been found that epigenetic programming of GR occurs in mammary carcinogenesis and plays a role in tumor progression by decreasing GR gene expression. BRCA1 gene expression levels are also decreased in some subjects with lower GR gene expression. Specifically, GR and BRCA1 mRNA levels were assayed in a small cohort of normal and tumor human breast samples. In both normal and tumor tissue, GR and BRCA1 gene expression levels were correlated and expression of both genes was reduced in tumor compared to normal tissue. The methylation status of the GR promoter in breast samples was assessed to see if GR was epigenetically regulated in breast cancer. While not detectably methylated in normal tissue, it was found that the GR proximal promoter was methylated in 13% of tumor samples. GR expression in these tumors was particularly low and loss of GR expression was correlated with methylation of the proximal GR 5 region. Overall, these results show that lower GR gene expression levels with associated decreased BRCA1 gene expression in tissues may be a predisposing factor for breast cancer. Furthermore, loss of GR gene expression by methylation of the promoter in tumors is a frequent event indicative of GR serving as a tumor suppressor in breast tissue.

Figure 1:
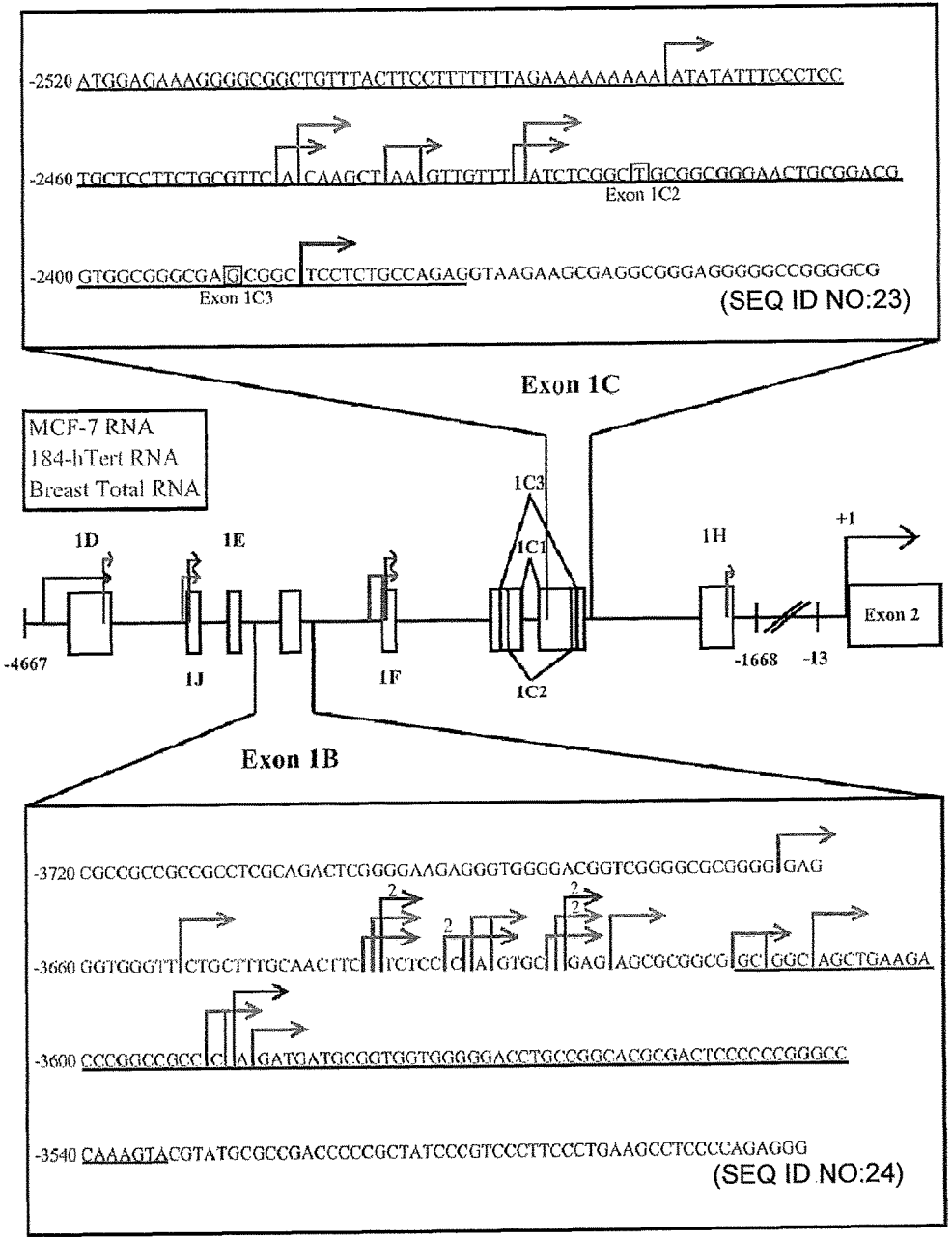
FIG. 1 shows rapid amplification of cDNA ends (5' RACE) for MCF-7, hTert and Total Breast RNA of the GR gene. 5' RACE was performed for MCF-7, 184-hTert and total breast RNA and the products were cloned into pBS+ vector before being transformed into DH5α electrocompetent bacteria. Positive clones were sequenced. All arrows begin at the most 5' end of the cDNA sequence of individual samples and all analyzed sequences continue to the 3' end of their associated alternative exon followed by the sequence of the common acceptor splice site immediately upstream of exon 2. Arrows with a number overhead indicate the number of samples sharing the same sequence. Sequence-specific information for exon 1B is underlined and shown in its entirety as well as a portion of exon 1C, including the common 3' site for all three of its transcript variants and the splice sites for exons 1C2 and 1C3 indicated by the squared nucleotide. In total 9 MCF-7, 14 184-hTert and 17 breast total RNA samples were sequenced. Of these, the majority (60%) were exon 1B (5/9, 10/14, and 9/17 respectively). The second most frequent exon was exon 1C1 (1/9, 2/14, and 5/17 respectively) at markedly lower abundance (20%). One sample obtained from breast total RNA mapped to exon 1A3 of the distal promoter and is not included in this figure.

Experiments were conducted to definitively determine which GR alternative first exons are present in breast RNA and in what abundance. Rapid amplification of cDNA ends (i.e., 5' RACE) was conducted using normal breast RNA, as well as RNA from a non-malignant (184-hTert) and malignant mammary epithelial cell line (MCF-7). Sequence analysis of the 5' RACE products showed that the majority of GR RNA sequences mapped to exon 1B for total human breast (9/17 total clones), 184-hTert (9/17 clones), and MCF-7 RNA (5/9 clones). This indicated that exon 1B was the primary alternative exon expressed in both normal and malignant breast GR mRNA transcripts. The next most frequent was exon 10, although at markedly lower abundance (5/17 breast total RNA, 2/14 184-hTert, 1/9 MCF-7). All exons detected were located in the proximal promoter, with the exception of one exon, 1A3 sequence (see FIG. 1). This indicated that in the breast, the proximal promoter is predominantly responsible for GR expression. The tissue heterogeneity of the human breast was found not to affect the reliability of the 5' RACE reaction, as results for total normal breast RNA were consistent with the clonal mammary epithelial breast cell lines.

Experiments were then performed to determine if GR and BRCA1 gene expression correlated in normal and tumor primary human breast tissue. Relative GR and BRCA1 gene expression levels in normal and tumor tissue from 59 breast cancer patients were determined by qRT-PCR. It was found that GR and BRCA1 gene expression was variable between patients as represented by a broad distribution of values. These genes were also found to be positively correlated in both normal ($r=0.5964$, $p<0.0001$) and tumor ($r=0.5108$, $p<0.0001$) tissue (see FIGS. 2A and 2B). GR gene expression in normal tissue was found to be unrelated to its expression in tumor tissue ($r=0.01169$, $p=0.9299$) (FIG. 2C). BRCA1 gene expression in normal breast tissue was weakly correlated with levels in tumor tissue (FIG. 2D), although the correlation was found to be statistically significant ($r=0.4216$, $p=0.001$). This indicates that GR and BRCA1 gene expression is uncoupled from normal to tumor tissue and that the transformation process may be independent of the initial state of gene expression in the normal breast.

Figure 3A:
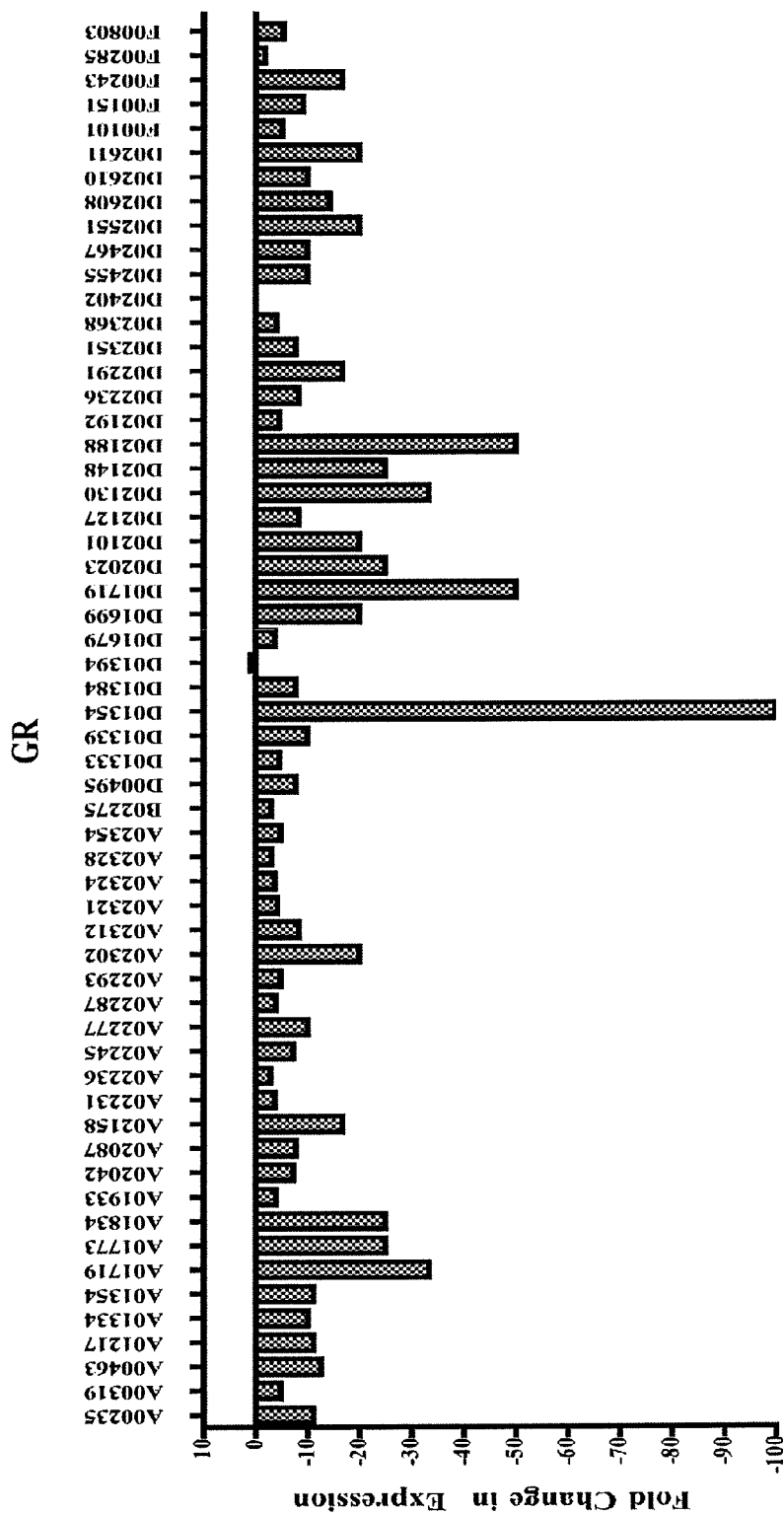
FIGS. 3A and 3B show the fold change in GR (FIG. 3A) and BRCA1 (FIG. 3B) gene expression from normal to tumor tissue. Normalizing tumor tissue gene expression to matched normal tissue expression and calculating the fold difference determined the fold change in gene expression for each patient.
Figure 3B:
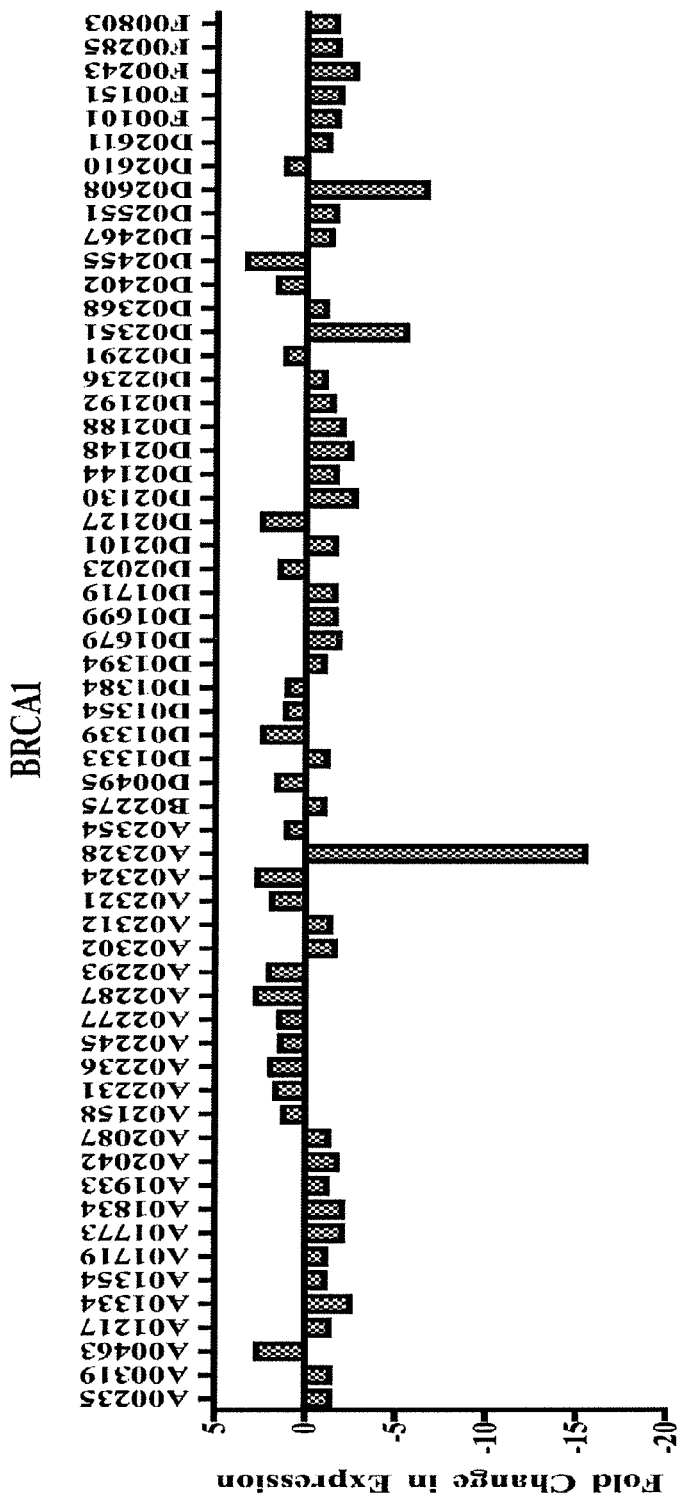

To determine whether patients showed any significant changes in gene expression, the fold difference in gene expression for GR and BRCA1 was also calculated from normal to tumor tissue. GR expression was lower in all tumors compared to normal tissue for all patients except one (D01394 fold response=1.07) with an average decrease in GR expression of 13.81-fold (FIG. 3A) (standard deviation=15.78). Based on these results, loss of GR expression appears to be a ubiquitous and important event in breast tumor development. Changes in BRCA1 gene expression were more variable and 21 patients had increased BRCA1 gene expression in tumor tissue with an average increase of 1.79-fold (standard deviation=0.67). The majority of tumors (38/59) had decreased BRCA1 transcription although the average decrease was markedly smaller at 2.22-fold (standard deviation=2.48) (see FIG. 3B) than was seen for GR expression.

A methylation detection assay, referred to herein as methylated DNA immunoprecipitation(MeDIP)-qPCR, was developed to determine promoter-wide GR methylation status in human breast cell lines and primary tissues. Methylated DNA (MeDNA) was enriched using MeDIP and cycle threshold (Ct) values for specific probes were obtained by qPCR. The cycle threshold (Ct) is determined when carrying out quantitative PCR (qPCR). The sample is added to a PCR reaction with appropriate PCR primers in the presence of a DNA binding dye such as Syber green in a thermocycler able to detect this fluorescence such as a Biorad CFX96 Touch™ Real-Time PCR Detection System. As amplification continues, product builds up in the chamber and is detected as increasing fluorescence. This produces a sigmoidal fluorescence curve where the reaction passes through an exponential phase and then into a plateau phase. The cycle threshold (Ct) is defined as the point where the amplification passes through the greatest rate of change and is typically set just above the background level of fluorescence. The difference between the values of two samples is the delta Ct ($\Delta$Ct) and represents the log base 2 difference in values.

The difference between methylated and flow-through DNA fractions ($\Delta$Ct) was used as a quantitative measure of DNA methylation as well as a means of controlling for the amount of DNA in each sample. Small $\Delta$Ct values indicate high levels of methylation whereas large $\Delta$Ct values, or no Ct value obtained for the MeDNA fraction, are an indication of little or no methylation for the region amplified. The CpG island at the 3' end of the SLC25A37 gene was used as a positive methylation control and the TATA-binding protein (TBP) promoter CpG island, unmethylated in all cells, was used as the negative control (Rauch, et al. (2006) *Cancer Res.* 66:7939-47). The MeDIP assay does not enrich for all methylated DNA in a sample as roughly 50% of SLC25A37 DNA was found to remain in the flow-through fraction, as evidenced by similar Ct values for the MeDIP and flow-through in tumor samples (average $\Delta$Ct=1.48), although this was more variable in normal tissue samples (average $\Delta$Ct=7.22). While the assay lacks enrichment efficiency, it is specific as only SLC25A37 and not TBP was amplified in the methylated DNA fraction, providing evidence that the MeDIP assay was capable of successfully enriching methylated DNA without contamination from unmethylated sequences.

Figure 4:
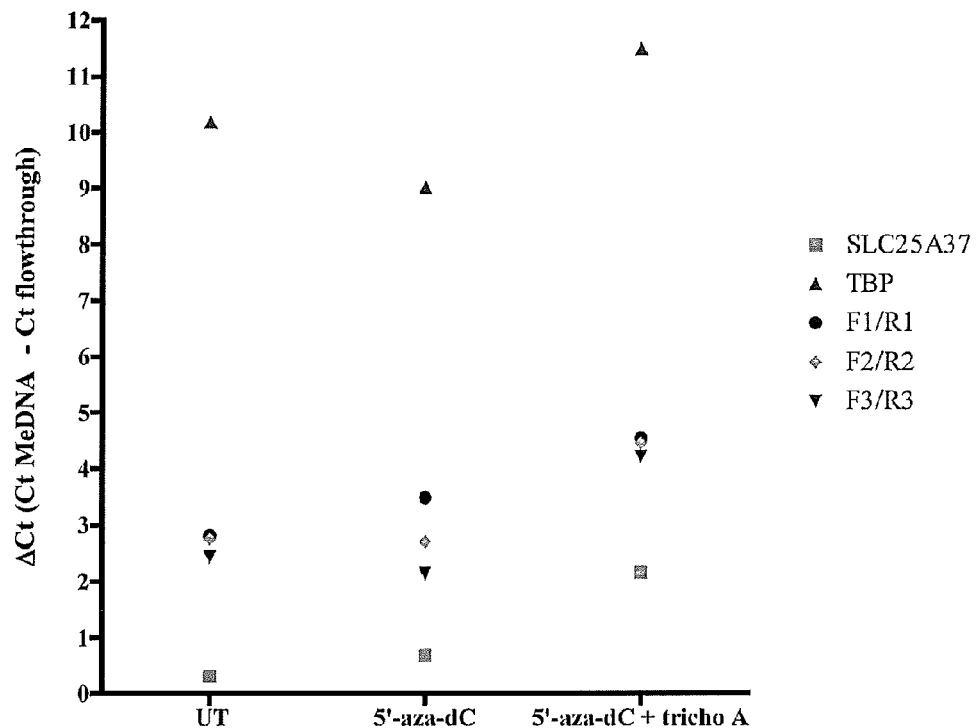
FIG. 4 shows validation of the methylated DNA immunoprecipitation (MeDIP or mDIP)-qPCR assay using hypomethylated UACC-3199 cells. UACC-3199 cells methylated at the BRCA1 promoter were treated with 50 ng/µL 5'-aza-dC alone or in combination with 50 ng/µL trichostatin A to hypomethylate genomic DNA. Flow-through and MeDNA fractions from treated and untreated (UT) cells were amplified by qPCR using three primer sets specific to the BRCA1 promoter (F1/R1, F2/R2, F3/R3) as well as SLC25A37 and TBP. ΔCt was calculated for each primer set. TBP had relatively consistent ΔCt values regardless of treatment (ΔCt=10.19, 9.02, and 11.50 for untreated, 5'-aza-dC alone and in combination with trichostatin A respectively). Treatment with 5'-aza-dC and trichostatin A was the most successful in hypomethylating UACC-3199 DNA as ΔCt values are largest for SLC25A37, F1/R1, F2/R2, and F3/R3 in this sample (ΔCt=2.17, 4.55, 4.46, and 4.22 respectively) compared to the untreated (ΔCt=0.31, 2.82, 2.76, and 2.44) and 5'-aza-dC treated cells (ΔCt=0.69, 3.49, 2.71, 2.15).

The MeDIP-qPCR method was validated using UACC-3199 breast cancer cells known to be methylated at the BRCA1 promoter (Xu, et al. (2010) *Breast Cancer. Res. Treat.* 12):593-601). Cells were treated alone or in combination with 5'-aza-2-deoxycytidine (5'-aza-dC) and trichostatin A, or with vehicle controls. Genomic DNA was collected and analyzed by MeDIP-qPCR using primers specific to the BRCA1 promoter. In agreement with previous findings (Wei, et al. (2005) *Cancer Res.* 65:10692-9), the combination of 5'-aza-dC and trichostatin A was the most successful at hypomethylating the BRCA1 promoter, as well as SLC25A37 (FIG. 4). Based on the changes in $\Delta$Ct values observed as a result of hypomethylation it was determined that the MeDIP-qPCR method is capable of identifying methylated regions as well as detecting changes in methylation levels.

Figure 5:
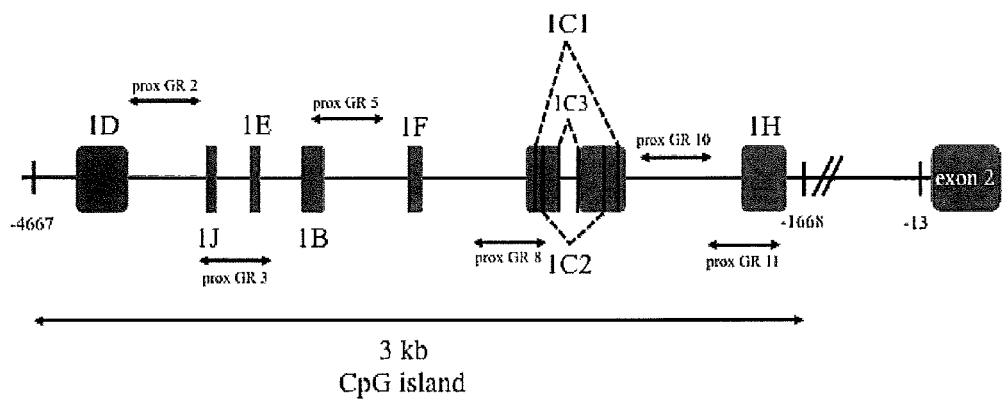
FIG. 5 shows the target location of qPCR primers in the GR proximal promoter. The GR proximal promoter is located in a kbp CpG island approximately 5 kbp upstream of the translation start site and contains seven alternative first exon sequences. Primers were designed spanning the proximal promoter and used for subsequent MeDIP-qPCR analysis. Relative to the translation start site, located in exon 2, the prox GR 2 primer set amplifies a 261-bp region from −4287 to −4027, prox GR 3 amplifies a 283-bp region from −4046 to −3764, prox GR 5 amplifies a 209-bp region from −3549 to −3339, prox GR 8 amplifies a 204-bp region from −2868 to −2665, prox GR 10 amplifies a 298-bp region from −2294 to −1997, and prox GR 11 amplifies a 222-bp region from −2017 to −1796.
Figure 6A:
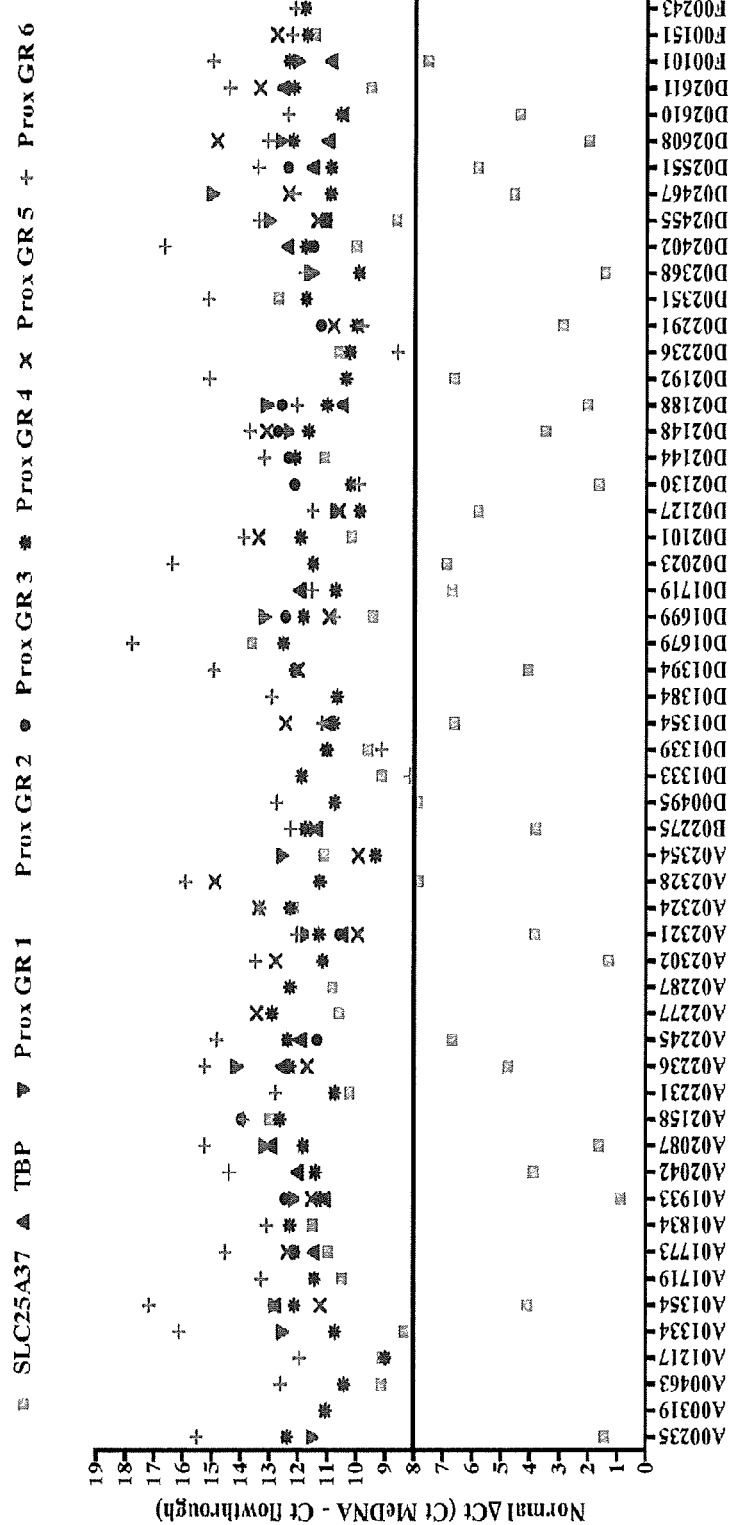
FIGS. 6A and 6B show MeDIP-qPCR of matched normal and tumor tissue for 59 breast cancer patients. Flow-through and MeDNA extracted from 59 homogenized matched normal and tumor tissues from breast cancer patients was amplified by qPCR using primers specific to the GR proximal promoter (prox GR 2, 3, 5, 8, 10, and 11) as well as SLC25A37 and TBP. The ΔCt was calculated for each primer set. Samples were considered as being methylated at the GR proximal promoter if three primer sets had ΔCt values below eight. The results in FIG. 6A indicate that no normal patient tissues samples were methylated. Four normal tissue samples (A02293, A02312, F00285, F00803) did not yield enough DNA for qPCR analysis and were excluded from analysis. The results in FIG. 6B show that eight matched tumor samples (A01719, B02275, D01354, D01384, D02130, D02291, D02368, D02551), boxed in the figure, were methylated at the GR proximal promoter. One tumor tissue sample (A02302) did not yield enough DNA for qPCR analysis and was excluded from analysis.
Figure 6B:
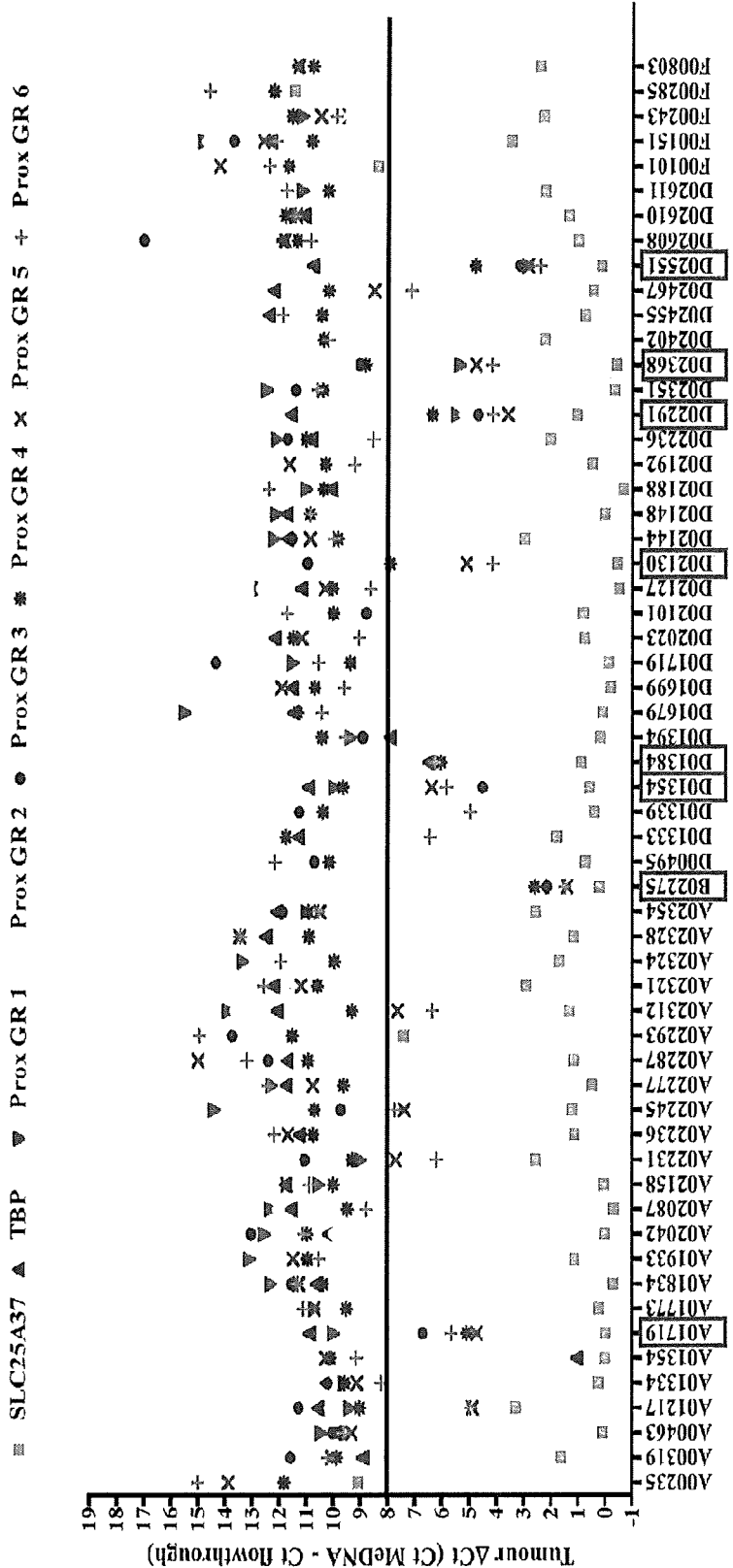

MeDIP-qPCR analysis was performed for all normal and tumor patient tissue samples using six primer sets spanning the GR proximal promoter (see FIG. 5), as 5' RACE revealed almost exclusively proximal promoter first exon usage in breast tissue. Based on $\Delta$Ct clustering with either TBP or SLC25A37, tissues with a minimum of three out of six primer sets with $\Delta$Ct values below eight were considered methylated at the GR proximal promoter. All assayed normal patient samples were unmethylated at the GR proximal promoter (see FIG. 6A) and a total of eight tumor samples (13%) were methylated (see FIG. 6B). The characteristics of the patients with methylated tumors are summarized in Table 1. Six of the eight samples methylated at the GR proximal promoter were ER+/PR+/Her2−, one was ER−/PR−/Her2−, and the last was ER+/Her2+ with unknown PR expression. It was observed that the prox GR 3 primer set was methylated in seven of the eight methylated samples and that the prox GR 5 primer set was methylated in five. The prox GR 3 and prox GR 5 primer sets flank the exon 1B promoter sequence, the predominant alternative first exon in breast tissue, and so methylation of these regions may be important for the regulation of GR transcription.

As will be understood by the skilled artisan upon reading this disclosure, for other trials an alternative $\Delta$Ct value above or below eight could be selected based upon observed clustering.

To determine whether GR promoter methylation had an effect on GR or BRCA1 transcriptional activity, gene expression was analyzed in methylated vs. unmethylated tumor samples (Table 1). Eight breast cancer patients had tumors with $\Delta$Ct less than 8 for at least three of six GR proximal promoter primers. Three tumors were methylated at every region spanned by the six primers (B02275, D02291, D02551). Patients with methylated tumors ranged from 50 to 89 years of age and the majority were ER+/PR+/Her2− (A01719, D01354, D01384, D02130, D02291, D02551). The Relative Expression of GR and BRCA1 for each sample were determined by normalizing gene expression to sample A00235 normal tissue. Average relative GR expression was 0.20 and average relative BRCA1 gene expression was 1.80 in the methylated samples.

TABLE 1

| Sample | Methylated Primer Sets | Age | Hormone Receptor Status | GR | BRCA1 |
|---|---|---|---|---|---|
| A01719 | 3, 5, 8, 10, 11 | 85-89 | ER+/PR+/Her2− | 0.10 | 1.62 |
| B02275 | 2, 3, 5, 8, 10, 11 | 55-59 | ER−/PR−/Her2− | 0.05 | 1.22 |
| D01354 | 3, 5, 10, 11 | 75-79 | ER+/PR+/Her2− | 0.05 | 2.49 |
| D01384 | 3, 8, 11 | 50-54 | ER+/PR+/Her2− | 0.62 | 3.44 |
| D02130 | 8, 10, 11 | 60-64 | ER+/PR+/Her2− | 0.09 | 0.87 |
| D02291 | 2, 3, 5, 8, 10, 11 | 75-79 | ER+/PR+/Her2− | 0.13 | 2.25 |
| D02368 | 2, 3, 10, 11 | 55-59 | ER+/PR$_{unk}$/Her2+ | 0.47 | 1.68 |
| D02551 | 2, 3, 5, 8, 10, 11 | 65-69 | ER+/PR+/Her2− | 0.11 | 0.86 |

Figure 7A:
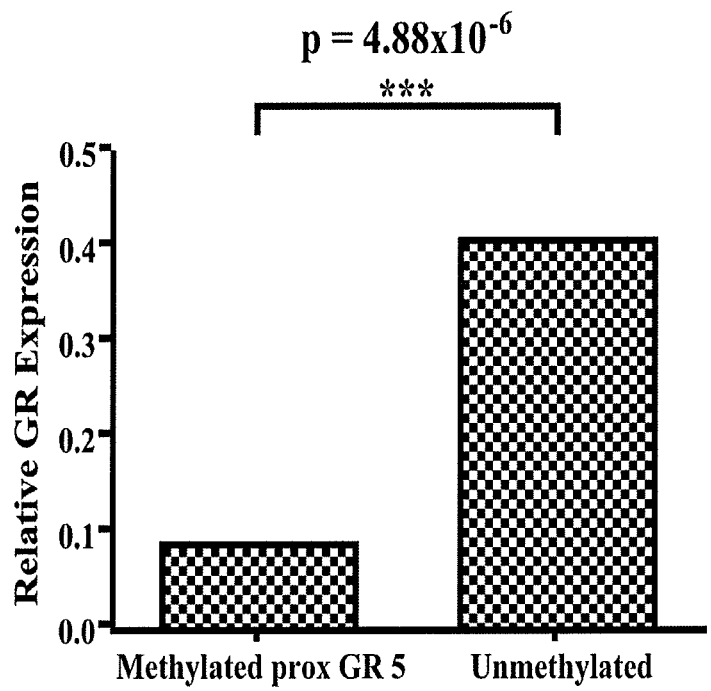
FIGS. 7A and 7B show GR and BRCA1 expression in samples methylated at the prox GR 5 region. Statistical analysis of gene expression data obtained by qRT-PCR by T-test was used to determine whether methylation of breast tumors significantly altered gene expression.
Figure 7B:
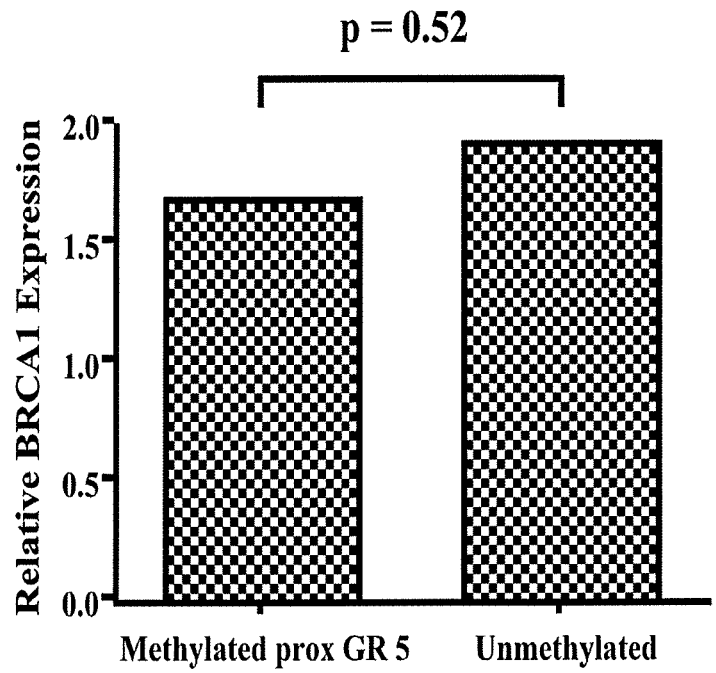

Initial statistical analysis revealed that there was no significant difference in GR (p=0.055) or BRCA1 (p=0.746) gene expression between tumors methylated and unmethylated at the GR proximal promoter. As methylation of the prox GR 3 and prox GR 5 regions were identified as a potentially important regulator of GR expression, statistical analysis was also conducted for tumors methylated at either prox GR 3 or prox GR 5. It was found that prox GR 3 methylation status did not significantly affect GR transcription (p=0.111), but tumors methylated at prox GR 5 had significantly lower GR expression than tumors unmethylated at this region (p=4.88×10$^{-6}$), identifying prox GR 5 as important for the regulation of GR transcription (see FIG. 7A). Due to potential correlation of GR and BRCA1 gene expression, it was also thought that prox GR 5 methylation might have an effect on BRCA1 gene expression levels. However, BRCA1 gene expression was not significantly reduced in tumors methylated at prox GR 5 (p=0.520) compared to unmethylated cancers (see FIG. 7B). In these tumors, BRCA1 gene expression appeared to be independent of GR methylation status.

Estrogen receptor positive (ER+) breast tumors are generally considered to have a good prognosis in that they tend to be less aggressive, they are thought to respond to antiestrogen based therapies, and they generally present at an earlier stage. ER+ tumors are by far the most prevalent tumors and represent some 60% of all breast cancer, and thus represent a large population of women at risk of relapse. Five year relapse rates are currently in the area of 25% having benefited from the use of optimal polychemotherapy and the introduction of tamoxifen and aromatase inhibitors such as, for example, AROMASIN (exemestane; Pfizer Inc, NY, USA) and ARIMIDEX (anastrozole; Astrazeneca, London, UK), which have reduced relapse rates by almost 50%. Through analysis of several public databases where both microarray and patient outcome data was available for breast cancer patients, Pan et al. classified tumors based on ER, HER2 and GR expression levels (Cancer Res. 2011 71(20): 6360-70). Further, Pan et al. disclosed that high GR expression levels were correlated with poor outcome in ER− tumors while low GR expression levels were associated with poor outcome in ER+ patients (Cancer Res. 2011 71(20): 6360-70). Examining patients that had been treated with tamoxifen identified an even greater difference in relapse-free survival between patients with high and low GR expression levels (Pan et al. Cancer Res. 2011 71(20):6360-70). Based upon findings described herein demonstrative of the frequency of GR methylation, it is now believed that GR methylation is a useful biomarker, when measured alone or in combination with determination of the tumor being ER− or ER+, to prognosticate outcome in women with breast cancer. Varying treatments for breast cancer can be selected and administered based upon GR methylation in a subject and their prognosticated outcome.

Figure 8:
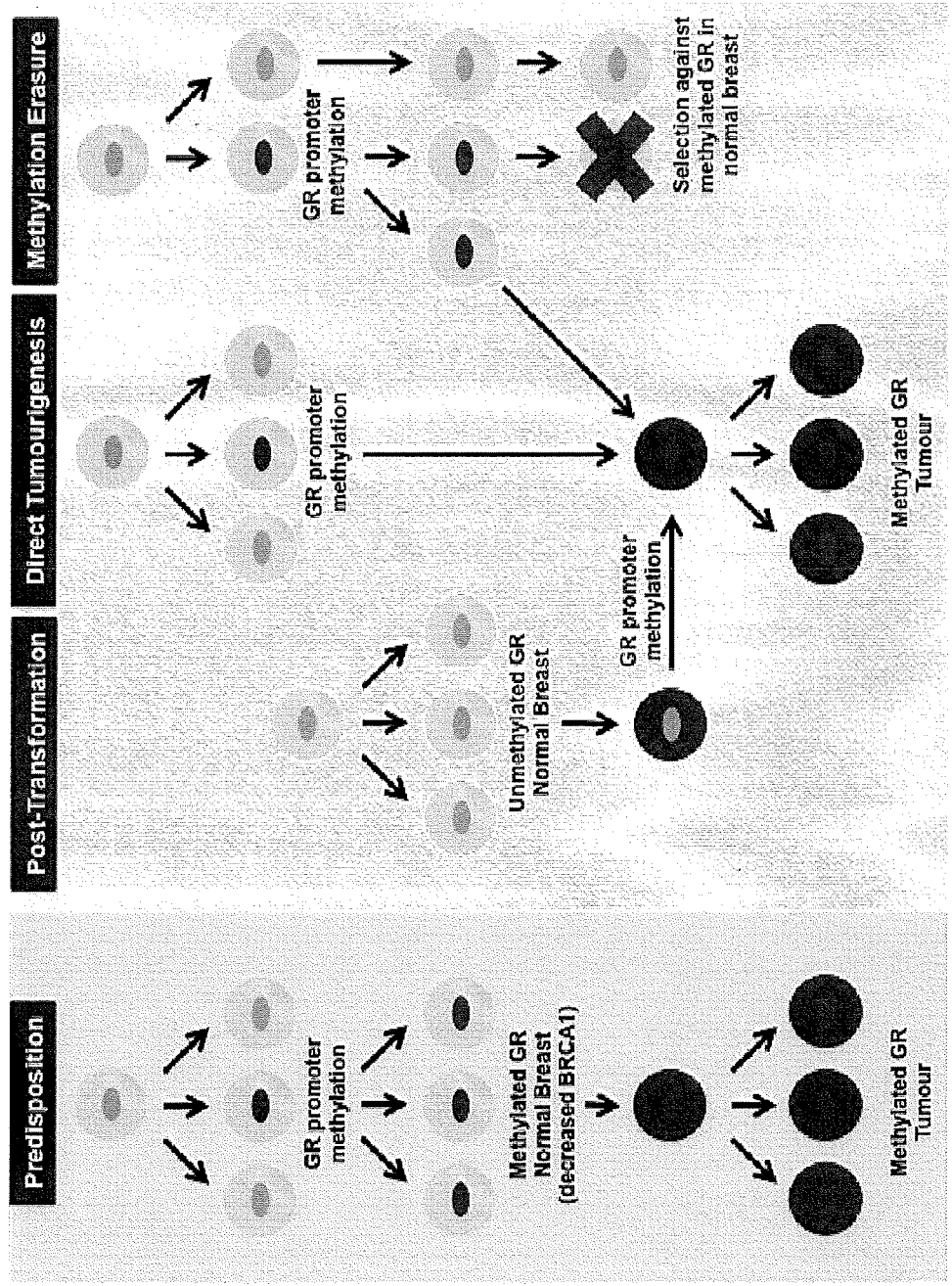
FIG. 8 shows models of GR methylation. In the predisposition model, GR promoter methylation occurs in response to early stressful life events and gives rise to a population of cells methylated at the GR promoter in the normal breast with decreased BRCA1 expression that is predisposed to transform and gives rise to a methylated GR tumor. In Direct Tumorigenesis, GR promoter methylation occurs in response to early life events but gives rise to a tumor directly without contributing to a population of methylated normal breast cells. In Post-Transformation, GR promoter methylation occurs only as a result of cancer progression and is not a predisposing factor for breast cancer. In Methylation Erasure, GR methylation occurs and contributes to a population of methylated normal cells that can then give rise to a tumor. Cells methylated at the GR promoter are selected against in normal tissue by processes such as pregnancy or menopause that involve physiological changes in the breast.

The findings herein have thus resulted in a new understanding of GR involvement in breast cancer development. According to the Predisposition Model, GR promoter methylation would occur due to stress and result in a population of methylated cells in the normal breast. These cells would have lower BRCA1 gene expression levels and be predisposed to transformation, resulting in a tumor with methylated GR. Based on MeDIP-qPCR analysis of 59 patient samples that detected no methylation in normal tissue, three new possible models have been developed. In the Direct Tumorigenesis model, GR promoter methylation occurs in normal tissue but the methylated cell goes on to be transformed and become a methylated GR tumor, leaving no methylated GR cells behind in the normal tissue. In the Post-Transformation model, GR methylation only occurs as a part of cancer progression and not as a predisposing factor. In the Methylation Erasure model, GR promoter methylation occurs in the normal breast and results in a population of methylated cells predisposing an individual to develop a tumor (see FIG. 8). Methylated GR cells not part of the tumor may be erased, or selected against, during physiological changes in the normal breast associated with pregnancy or menopause. Studies in the mouse mammary gland have found that BRCA1 levels are high during pregnancy, low during lactation, and high again during involution (Mueller & Roskelley (2003) *Breast Cancer Res.* 5:45-52). Not wishing to be bound by thereof, this suggests that during involution there is selection against cells with low BRCA1 expression, which would include those cells methylated at the GR proximal promoter. Multiple pregnancies have also been shown to have a protective effect against breast cancer (RR=0.8, 95% CI=0.7-1.0) (LaVecchia, et al. (1993) *Internat. J. Cancer* 53:215-9) and it can be postulated that a loss of cells affected by early life GR promoter methylation may account for this observed effect. Of the eight tumors methylated at the GR proximal promoter, five patients had previously had children, which could explain the lack of normal tissue methylation in these women.

Given that it has now been found that GR methylation with a consequent reduction in GR gene expression levels, as well as reduction in BRCA1 gene expression levels in some subjects, is correlated with breast cancer, methylation of the GR promoter and GR and BRCA1 gene expression levels can be used in the diagnosis and prognosis of breast tumorigenesis.

Accordingly, certain aspects of this invention relate to methods for diagnosing breast cancer or prognosticating outcome of a subject diagnosed with breast cancer by detecting methylation of the glucocorticoid receptor promoter.

As is known in the art, the glucocorticoid receptor (GR, GCR or NR3C1 (nuclear receptor subfamily 3, Group C, member 1)) is the receptor to which cortisol and other glucocorticoids bind. The gene encoding GR is located on chromosome 5: 142,657,496 to 142,815,077 (reverse strand) and is provided under GENBANK Accession No. AY436590.1. The promoter and 5'-UTR nucleic acid of this sequence are shown in FIG. 9.

For purposes of the present invention, methylated GR gene and/or promoter may be referred to herein simply as methylated GR, and cells or tumor containing methylated GR gene and/or promoter may be referred to as methylated GR cells or methylated GR tumor.

For purposes of the present invention, the glucocorticoid receptor proximal promoter region 5 may be referred to herein as proximal GR 5, prox GR 5, prox 5 GR or prox 5 region. Similarly, the glucocorticoid receptor proximal promoter region 3 may be referred to herein as proximal GR 3, prox GR 3, prox 3 GR or prox 3 region.

"Methylation", as used herein refers to DNA having one or more residues that are methylated. For example, in all vertebrate genomes some of the cytosine residues are methylated. As demonstrated herein, DNA methylation affects GR and BRCA1 gene expression and is an epigenetic marker for breast cancer. In accordance with the methods described herein, methylation level or content as well as the pattern of methylation can be determined.

"Methylation content" or "methylation level", as used herein, refers to the total number of methylated residues, such as the total number of methylated sites on the DNA of interest, such as a gene or a relevant fragment of a gene. In particular, "methylation content" is a measure of the total fraction of nucleotide residues (e.g., cytosines) that are methylated. "Methylation level" refers to the average methylation occupancy at a particular cytosine residue.

"Methylation pattern" or "pattern of methylation", as used herein, refers to the distribution and location of methylated sites on the DNA of interest. For example, gene expression may be affected even when the methylation content does not change in situations where methylated regions or sites change or shift to different locations along the strand. In one aspect, aberrant methylation in one or more regions of the GR promoter results in a change in expression of GR and BRCA1 protein.

"Detecting" is used broadly to refer to a technique that, directly or indirectly, provides information about DNA methylation. Such techniques include those exemplified herein as well as conventional processes known in the art for detecting methylated DNA including, but not limited to, immunoprecipitation of methylated DNA (MeDIP), methylation specific binding protein columns, methylation-sensitive restriction digestion, methylation sensitive PCR, Matrix Assisted Laser Desorption/Ionization (MALDI) and time-of-flight mass spectrometry (TOFMS), Methylation-Specific PCR (MSP; Herman, et al. (1996) *Proc. Natl. Acad. Sci. USA* 93:9821-9826; U.S. Pat. No. 5,786,146), a fluorescence-based real-time PCR technique such as METHYLIGHT (Eads, et al. (1999) *Cancer Res.* 59:2302-2306), combined bisulfite restriction analysis (COBRA; Xiong & Laird (1997) *Nucleic Acids Res.* 25:2532-2534), and direct analysis of bisulfite converted DNA, e.g., through either sequencing (pyrosequencing or Sanger sequencing) or microarray analysis.

Immunoprecipitation of methylated DNA is based on the simple concept of using a monoclonal antibody raised against 5-methyl-cytosine (mC). Genomic DNA extracted from cells or tissue is fragmented through sonication or shearing to yield fragments on the order of 1 kbp or smaller. One fraction of the fragmented DNA is then denatured and immunoprecipitated with the mC antibody. The DNA is washed, and the precipitated DNA recovered. Usually, this methyl-enriched DNA is then run on a microarray versus the other fraction of the original "input" DNA from the sonication. The two DNA fractions are labeled with Cy3 and Cy5 fluorescent markers using standard kits, and the results assayed on the microarray to obtain a ratio (Weber, et al. (2005) *Nature Genetics* 37:853-62).

Methyl-sensitive digestion is another method to sort methylated from unmethylated parts from the genome. Restriction enzymes are sequence-specific, and some are sensitive to whether the DNA is methylated or not. For example HpaII and MspI are a pair of isoschizomers recognizing CCGG, wherein MspI is insensitive to methylated status and HpaII cuts only unmethylated recognition sites. Another enzyme of use is McrBC, which recognizes any pair of (A/G)$^m$Cs that are from 40-3000 bp apart, and cuts at one of the sites (Panne, et al. (1999) *J. Mol. Biol.* 290(1): 49-60). Genomic DNA is first fragmented, digested with the methylation-sensitive enzyme, then either amplified with recognition site-specific PCR or separated by size. Cleavage-based ligation is also possible, using primers that match the recognition site and amplify only fragments which were cut, i.e., amplifying the unmethylated fraction, e.g., as in HpaII tiny fragment Enrichment by Ligation-mediated PCR (HELP) (Khulan, et al. (2006) *Genome Research* 16(8): 1046).

Methylation-specific PCR uses a combination of bisulfite treatment and primer design to determine methylation status of a given DNA locus. After bisulfite treatment, any unmethylated cytosine residue is deaminated, converting it to uracil. Methylated cytosines are protected from deamination, so they are kept as cytosines. This alters the sequence of the treated DNA in a predictable, methylation-dependent way. By designing primers that amplify either unchanged cytosines or cytosines converted to uracil, the methylation status of the original genomic DNA is determined, based on which primers give product. This technique is particularly specific and only requires relatively small amounts of genomic DNA (as few as 100 cells).

Separation of methylated from unmethylated DNA can also be accomplished by taking advantage of the natural ability of certain DNA-binding proteins to differentiate between methylated and unmethylated DNA. For example, using a recombinant His-tagged version of the methyl binding domain (MBD) of MeCP2, and attaching it to a nickel-agarose matrix, a methyl-sensitive stationary phase for a column is constructed (Cross, et al. (1994) *Nature Genetics* 6(3):236-244). Genomic DNA is then sheared or cleaved by MseI, which cuts in A/T-rich regions, yielding small C/G-rich fragments which may be run through the column and purified on the basis of the strength of binding. This allows for fractions to be extracted which vary in the level of methylation.

Alternatively, methylated DNA can be sorted and detected using a synthetic nanopore as described in U.S. Pat. No. 8,394,584, which is incorporated herein by reference in its entirety. Using this technology, heterogeneous DNA populations are separated based on DNA methylation by providing a membrane having a nanopore through which an electric field is applied. DNA of interest is introduced, and for a given threshold voltage across the nanopore, only DNA having a methylation parameter of interest may transit the pore, thereby facilitating detection, characterization, or separation of DNA based on methylation.

As indicated herein, analysis of GR promoter methylation indicated that, although not detectably methylated in normal tissue, breast tumor samples were methylated at the GR proximal promoter. Accordingly, in some embodiments, the presence or level of methylation of the entire GR promoter is determined. As further demonstrated herein, the methylation of the prox GR 5 region resulted in significantly decreased GR transcription. Accordingly, in other embodiments, the presence or level of methylation of the prox GR 5 region is determined. Tumorigenicity is also demonstrated herein to be associated with methylation of the prox GR 5 region, the prox GR 3 region, and other regions of the GR gene. Accordingly, in some embodiments, the presence or level of methylation of the prox GR 5 region and/or the prox GR 3 region and/or other regions of the GR gene is determined, wherein such methylation is indicative of breast cancer diagnosis and/or prognosis.

In accordance with one aspect of the invention, the detection of GR promoter methylation is performed in a sample obtained from the subject. Examples of samples in which GR promoter methylation can be detected in accordance with the present invention include, but are not limited to, breast tissue, blood, serum, plasma, urine and ductal lavage or nipple aspirates (Suijkerbuijk et al. Pathobiology 2008; 75(2):149-52). In some embodiments, detection of GR promoter methylation is performed in a cell-free system.

For the purposes of this invention, the term "subject" is intended to include any mammal (e.g., horses, dogs, humans). In a preferred embodiment, the subject is a primate. In an even more preferred embodiment, the primate is a human.

The term "obtaining" is intended to include recovery of a sample from a subject in a way such that the methylated GR promoter is retained in a form that can be detected by one or more of the methods described herein. Samples can be obtained from a subject using methods known in the art. For example, a breast tissue sample can be a breast biopsy sample or a sample of fluid obtained by breast duct lavage. In general, the sample can be obtained from a subject diagnosed with breast cancer or a subject suspected of being at risk of having breast cancer (e.g., because of environmental factors or family history). Alternatively, the sample can be obtained from a subject that has been treated for breast cancer, wherein prognosis is desired.

Detection of GR promoter methylation can be carried out directly on the sample, or the sample can be manipulated to, e.g., extract all or a portion of the DNA. In particular embodiments, a DNA sample is isolated from the sample. A "DNA sample" may be any material obtained from a subject that provides DNA of interest, including genomic DNA, at least a portion of the DNA genome, a fragment of the DNA genome containing a contiguous sequence of DNA, such as a portion of the GR gene including the GR promoter. DNA isolation from tissue samples is routinely carried out in the art and any method can be used as long as the methylation state of the DNA is retained.

Upon detecting of the presence or level of GR promoter methylation in a sample, said presence or level can be compared with a control. For example, when the level of methylation of the GR promoter as detected above is higher than the level of the methylation of the corresponding genomic DNA in normal cells, it can be determined that the subject has breast cancer. In the context of levels of GR promoter methylation in a sample from a subject, a higher level relative to a control value refers to a level that is statistically significant or significantly above levels found in the control value or tissue from a healthy subject. The term "statistically significant" or "significantly" refers to statistical significance and generally means a two standard deviation (2SD) above normal, or higher.

Alternatively, the level of GR promoter methylation can be expressed as the methylation frequency of the GR promoter. "The methylation frequency of the GR promoter" means the percentage (%) of methylated cytosine, guanine, adenine and thymine in DNA in the GR promoter. Such frequency can be expressed with numbers from 0% to 100%. For example, when cytosine is methylated in all DNA molecules at a single sequence, the methylation frequency of the sequence is 100%. On the other hand, when cytosine is demethylated in all DNA molecules at a single sequence, the methylation frequency of the CpG sequence is 0%. As for the methylation frequency of the GR promoter, when the methylation frequency of two or more regions is obtained, the methylation frequencies of individual regions may be added up, and the total value may be then divided by the number of the regions to obtain a mean value. In accordance with this aspect, when the methylation frequency of a subject is 20%, 30%, 40%, 50% or more, 60% or more, 70% or more, 80% or more, or 90% or more, it can be determined that the subject has or is at risk of having breast cancer.

Another aspect of the present invention relates to a method for prognosticating risk and/or outcome of a subject diagnosed with breast cancer. In this method, methylated glucocorticoid receptor promoter indicative of the outcome of the subject is detected. This aspect of the present invention may further comprise selecting and/or administering a treatment for breast cancer based upon the prognosticated outcome and/or risk.

When prognosticating outcome, a poor prognosis may be concluded from the presence of detectably higher levels of GR promoter methylation in the sample of the subject compared to the control value. Detectable differences in number of units from a cancerous sample and number of units from a control sample, e.g., an adjacent non-cancerous tissue, may be used to determine the prognosis of the patient from whom the samples were taken.

In this embodiment, the prognosis is further predicted by determination of the tumor being ER+ or ER−. Methods for determination of the tumor being ER+ or ER− can be performed routinely by those skilled in the art and are described, for example, by Gown (Mod. Pathol. 2008 May; 21 Suppl 2:S8-S15). Detecting a methylated GR promoter in the subject and determining the breast cancer to be ER+ is indicative of poor outcome in the subject. For this subject, more aggressive therapies and/or alternative therapeutics may be selected and/or administered. Examples of aggressive and/or alternative therapies for breast cancer subjects that could be given with standard therapy or in replacement of standard therapy include, but are not limited to, drugs targeting gene methylation, including demethylation agents and histone deacetylase (HDAC) inhibitors as described, for example, by Tan et al. (J Hematol Oncol. 2010 Feb. 4; 3:5), Wagner et al. (Epigenetics 2010 December; 1(3-4): 117-136) and Jankowitz et al. (Breast Cancer Res. 2011; 13(6):225). Examples of demethylation agents include the marketed products Dacogen (decitabine; Eisai Co., Tokyo, Japan), and Vidaza (Azacitidine; Celgene, NJ, USA), and products in development such as SGI-110 (Astex Pharmaceuticals California, USA). Examples of HDAC inhibitors include the marketed drugs Zolinza (vorinostat; Merck, NJ, USA) and Istodax (Romidepsin; Celgene NJ, USA), and drugs in development such as CI-994 (Tacedinaline; Pfizer, NY, USA), MS-275(SNDX-275, Entinostat; Syndax Pharmaceuticals, Massachusetts, USA), NVP-LAQ824 (Dacinostat, Novartis International AG, Basel, Switzerland), LBH-589 (Panobinostat, Novartis International AG, Basel, Switzerland), Mocetinostat (Methylgene Inc. Montreal, Quebec, Canada), PXD101 (Belinostat, Topotarget, Copenhagen, Denmark), Givinostat (Italfarmaco Cinisello Balsamo, Italy), PCI-24781 (Pharmacyclics California, USA) and CUDC-101 (Curis Massachusetts, USA).

Alternatively, a more positive prognosis indicative that standard treatment may be acceptable for the subject comprises detection of methylated GR promoter wherein a tumor is ER−. As ER− is still generally an indicator of poor outcome, however, a more aggressive and/or alternative therapies for breast cancer subjects such as described above may be selected and/or administered to these subjects as well.

Accordingly, the prognostic method of the present invention may further comprise the step of selecting a treatment to be administered to the subject and/or the step of administering the selected therapy to the subject.

In accordance with methods pertaining to prognosticating outcome of a subject diagnosed with breast cancer, certain embodiments further include measuring the level of BRCA1 gene expression in the subject, e.g., using one or more of the methods described below, wherein an abnormal level of BRCA1 gene expression in the subject as compared to the standard level is indicative of a poor outcome for the subject.

Other aspects of the invention relate to methods for diagnosing breast cancer in a subject based upon the level of GR and/or BRCA1 gene expression in the subject. In accordance with such methods, the levels of GR and/or BRCA1 gene expression in the subject are determined and said levels are compared with standard levels of GR and BRCA1 gene expression, wherein a low level of GR gene expression as compared to the standard level and an abnormal level of BRCA1 gene expression in the subject as compared to the standard level is indicative of breast cancer. In certain embodiments, the levels of GR and BRCA1 gene expression are measured in a breast tissue sample, a ductal lavage sample or a nipple aspirate sample obtained from the subject, e.g., as described herein.

In one embodiment the level of GR protein is determined. In another embodiment, the level of BRCA1 protein is determined. For the purposes of this invention, the relative or absolute level of GR and/or BRCA1 protein may be determined. Any convenient technique for determining the level of GR and/or BRCA1 protein may be employed including, but not limited to, ELISA, western blot analysis, dot blot, immunohistochemistry, immunofluorescence and mass spectrometry. In one embodiment, gel electrophoresis following by immunoblot analysis, preferably western blot analysis is used. In general, western blot analysis is a three-step procedure commonly used to separate a mixture of proteins and then identify a protein of interest. The first step requires separating a protein mixture by electrophoresis on an SDS-polyacrylamide gel (SDS-PAGE). Next, the resolved proteins in the gel are transferred (by electroblotting) to a thin nitrocellulose membrane, which binds most proteins. In the final step, the protein or proteins of interest are detected on the protein-studded membrane. In a preferred embodiment, the protein-studded membrane is soaked in a solution of antibodies that are specific for the protein or proteins of interest. In one embodiment, antibodies in this solution can be labeled for easy detection of protein-bound antibodies. In another embodiment, the protein-bound antibodies can be detected using a second antibody that is specific for the first. This second antibody may be bound to a fluorescing enzyme or dye that is detected using radiographic film or a colorimetrically detectable enzyme such as horseradish peroxidase or alkaline phosphatase. Alternatively, a technique has been developed referred to as UNIBLOT (Pierce Chemicals) which allows the western blot to be performed directly on the gel without the need for transfer of the resolved proteins to a nitrocellulose or PVDF membrane.

Immunohistochemical and immunofluorescence analysis can also be conducted to semi-quantitatively detect the levels of GR and/or BRCA1 gene expression in a tissue sample compared to a control. In general, tissue section samples are overlaid with a blocking solution and subsequently contacted with an anti-GR or anti-BRCA1 antibody. The sample sections are generally overlaid with the antibody solution for 10-20 hours and subsequently washed to remove unbound antibody. The protein/antibody complex is then detected either directly or indirectly as described above. Immunohistochemical techniques are well-known to those of skill in the art (see, e.g., "Methods in Immunodiagnosis", 2nd Edition, Rose and Bigazzi, eds. John Wiley & Sons, 1980; Oellerich (1984) *J. Clin. Chem. Clin. Biochem.* 22:895-904).

In addition, or in the alternative, the absolute or relative levels of GR and/or BRCA1 mRNA are detected or measured, for example, as exemplified herein or using methods well-known in the art. The most commonly used methods known in the art for the quantification of mRNA expression in a sample include northern blot analysis and in situ hybridization (Parker & Barnes (1999) *Meth. Mol. Biol.* 106:247-283); RNAse protection assays (Hod (1992) *Biotechniques* 13:852-854); PCR-based methods, such as reverse transcription polymerase chain reaction (RT-PCR) (Weis, et al. (1992) Trends in Genetics 8:263-264) or quantitative RT-PCR; and chip-based analysis. Alternatively, antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), gene expression analysis by massively parallel signature sequencing (MPSS), RNA-Seq as described, for example by Ozsolak and Milos (Nature Reviews 2011 12:87-98) and Nanostring as described, for example, at nanostring with the extension .com/ of the World Wide Web A sensitive and flexible quantitative method is RT-PCR, which can be used to determine mRNA levels in various samples. The results can be used to compare gene expression between sample sets, for example in normal and tumor tissues and in patients with or without drug treatment. The first step is the isolation of mRNA from a target sample. The starting material is typically total RNA isolated from human tumors, and corresponding normal tissues or cell lines. If the source of mRNA is a primary tumor, mRNA can be extracted, for example, from fresh, frozen or archived paraffin-embedded and fixed (e.g., formalin-fixed) tissue samples. General methods for mRNA extraction are well known in the art and are disclosed in standard textbooks of molecular biology, including Ausubel et al. (1997) *Current Protocols of Molecular Biology*, John Wiley and Sons. Methods for RNA extraction from paraffin embedded tissues are disclosed, for example, in Rupp & Locker (1987) *Lab Invest.* 56:A67 and De Andres et al. (1995) *BioTechniques* 18:42044. In particular, RNA isolation can be performed using purification kit, buffer set and protease from commercial manufacturers, such as Qiagen, according to the manufacturer's instructions. For example, total RNA from cells in culture can be isolated using QIAGEN RNeasy mini-columns. Other commercially available RNA isolation kits include MASTERPURE, Complete DNA and RNA Purification Kit (EPICENTRE, Madison, Wis.), and Paraffin Block RNA Isolation Kit (Ambion, Inc.). RNA prepared from tumor can be isolated, for example, by cesium chloride density gradient centrifugation.

The isolated RNA is then reverse transcribed into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers. For example, extracted RNA can be reverse-transcribed using a GENEAMP RNA PCR kit (Perkin Elmer, CA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQ-MAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers, e.g., those exemplified herein, are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 (Perkin-Elmer-Applied Biosystems, Foster City, Calif.), or LIGHTCYCLER (Roche Molecular Biochemicals, Mannheim, Germany).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real-time quantitative PCR, which measures PCR product accumulation through a dual-labeled fluorogenic probe (i.e., TAQMAN probe). Real-time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held, et al. (1996) *Genome Research* 6:986-994.

Further PCR-based techniques include, for example, differential display (Liang & Pardee (1992) *Science* 257:967-971); amplified fragment length polymorphism (iAFLP) (Kawamoto, et al. (1999) *Genome Res.* 12:1305-1312); BEADARRAY technology (Illumina, San Diego, Calif.; Ferguson, et al. (2000) *Analytical Chemistry* 72:5618); BEADSARRAY for Detection of Gene Expression (BADGE), using the commercially available LUMINEX100 LABMAP system and multiple color-coded microspheres (Luminex Corp., Austin, Tex.) in a rapid assay for gene expression (Yang, et al. *Genome Res.* (2001) 11:1888-1898); and high coverage expression profiling (HiCEP) analysis (Fukumura, et al. (2003) *Nucl. Acids. Res.* 31(16) e94).

Gene expression can also be measured using the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors and corresponding normal tissues or cell lines. Thus, RNA can be isolated from a variety of primary tumors or tumor cell lines. If the source of mRNA is a primary tumor, mRNA can be extracted, for example, from frozen or archived paraffin-embedded and fixed (e.g., formalin-fixed) tissue samples, which are routinely prepared and preserved in everyday clinical practice. Microarray analysis can be performed by commercially available equipment, following manufacturer's protocols, such as by using the AFFYMETRIX GENCHIP technology, or Incyte's microarray technology.

In certain embodiments, mRNA levels of GR and BRCA1 are measured in the breast tissue sample, a ductal lavage sample or a nipple aspirate sample obtained from the subject, e.g., as described herein.

Upon measuring or detecting the level of GR and/or BRCA1 gene expression in a subject or breast tissue sample, ductal lavage sample or nipple aspirate sample therefrom, said level is compared with a control or standard level, wherein a low level of GR gene expression as compared to the standard level and an abnormal level of BRCA1 gene expression in the subject as compared to the standard level is indicative of breast cancer. As used herein, a "low level" of GR gene expression is intended to mean a 2-fold, 3-fold, 4-fold, 5-fold, 10-fold or lower amount of GR gene expression in the test subject or tissue sample as compared to the amount of GR gene expression in the control or standard. As used herein, a "abnormal level" of BRCA1 gene expression is intended to mean a 2-fold, 3-fold, 4-fold, 5-fold, 10-fold or higher increase or decrease in amount of BRCA1 gene expression in the test subject or tissue sample as compared to the amount of BRCA1 gene expression in the control or standard. As demonstrated herein 60% of subjects with breast cancer exhibited low GR and low BRCA1 gene expression levels as compared to a standard or control while 40% of subjects with breast cancer exhibited low GR and high BRCA1 gene expression levels as compared to a standard or control. A standard or control can include a subject or tissue sample from a subject that is free of cancer or tissue from the test subject that is free of cancer, e.g., healthy breast tissue. Alternatively, control or standard levels can be an average of GR or BRCA1 gene expression levels obtained from a population of subjects known to be free of cancer. For purposes of comparison, a test sample and standard or control sample may be of the same type, which is obtained from the same individual. A standard or control can also be a standard sample that contains the same concentration of GR or BRCA1 gene expression that is normally found in a biological sample of the same type and that is obtained from a healthy individual, e.g., an individual who does not have cancer. For example, there can be a standard or control sample for the amounts of GR and/or BRCA1 gene expression normally found in a cell or tissue. By standard or control, it is also meant to be inclusive of a comparison to a data table containing average gene expression levels of GR and BRCA 1 in healthy individuals.

The diagnostic and prognostic methods as described herein can be used in early clinical assessment and/or diagnosis of breast cancer before or concurrent with conventional breast cancer diagnostic methods such as clinical exams and mammography. Using the methods of this invention, subjects having or at risk of having breast cancer can be identified and subsequently provided with an effective therapeutic regime for managing or treating breast cancer. In addition to early diagnosis, the methods of this invention can also be used for monitoring the progression of cancer in a subject by, e.g., monitoring GR promoter methylation and/or the presence or gene expression level of GR and/or BRCA1 in a cell or bodily fluid, e.g., in a cancerous cell or tumor, of the subject over time. An increase in GR promoter methylation, and/or decrease in GR expression, and/or decrease in GR expression and decrease or increase in BRCA1 expression, e.g., over time, indicates that the cancer is progressing.

Another aspect of the invention relates to a kit for diagnosing breast cancer and/or prognosticating outcome of a subject with breast cancer. In its simplest form, the kit of this invention includes a means for measuring a methylated glucocorticoid receptor promoter in a sample from a subject and optionally, a means for measuring a level of BRCA1 gene expression in a sample from a subject. Examples of means for measuring a methylated glucocorticoid receptor promoter include, but are not limited to, GR promoter-specific primers for use in methylation-specific PCR or MeDIP-qPCR. Means for measuring a level of BRCA1 gene expression include, but are not limited to, BRCA1-specific primers for use in PCR-based methods of detecting mRNA or anti-BRCA1 antibodies for use in immunological-based methods for detecting BRCA1 protein. Examples of primers useful in the methods and kits of the present include, but are not limited to those described in the Examples section of this patent application, as well as those set forth in Tables 2 and 3 below. As will be understood by the skilled artisan upon reading this disclosure, alternative primers for use in the kits and methods of the present invention can be routinely designed.

TABLE 2

Methylation-Specific Restriction Enzyme Primers

PROX GR 5

| | | |
|---|---|---|
| fwd: | 5'-GCTTTGCAACTTCTCTCCCAG-3' | (SEQ ID NO: 2) |
| rev: | 5'-GGTCGGCGCATACGTACTTT-3' | (SEQ ID NO: 3) |
| fwd: | 5'-TATCCCGTCCCTTCCCTGAA-3' | (SEQ ID NO: 4) |
| rev: | 5'-TCACTTCGAAAGGGGCTACG-3' | (SEQ ID NO: 5) |
| fwd: | 5'-CGTAGCCCCTTTCGAAGTGA-3' | (SEQ ID NO: 6) |
| rev: | 5'-GCTGAGCTGCGTGAGTGG-3' | (SEQ ID NO: 7) |

PROX GR 10

| | | |
|---|---|---|
| fwd: | 5'-CGCGGGAGCCTACAAACTTTTATTA-3' | (SEQ ID NO: 8) |
| rev: | 5'-GCTGCCCTTTCGTCACCG-3' | (SEQ ID NO: 9) |
| fwd: | 5'-TGGCCTCTTCCTCTCCCTC-3' | (SEQ ID NO: 10) |
| rev: | 5'-GTTCGACAGGGCTCCGC-3' | (SEQ ID NO: 11) |
| fwd: | 5'-AGGAACCTGACCTCGGACG-3' | (SEQ ID NO: 12) |
| rev: | 5'-CGAGGAATGAGAGGCTCGAA-3' | (SEQ ID NO: 13) |

TABLE 3

MSP Primers

PROX GR 5
Meth-specific

| | | |
|---|---|---|
| fwd: | 5'-TAGAGGGCGTGTTAGGTCGT-3' | (SEQ ID NO: 14) |
| rev: | 5'-GCCGAACCGAATTACGTA-3' | (SEQ ID NO: 15) |

Unmeth-specific

| | | |
|---|---|---|
| fwd: | 5'-TTAGAGGGTGTGTTAGGTTGT-3' | (SEQ ID NO: 16) |
| rev: | 5'-CCACCAAACCAAATTACATA-3' | (SEQ ID NO: 17) |

PROX GR 8
Meth-specific

| | | |
|---|---|---|
| fwd: | 5'-GTGGCGTCGTTTTTATTC-3' | (SEQ ID NO: 18) |
| rev: | 5'-AAATAAAAAAACGACGACG-3' | (SEQ ID NO: 19) |

TABLE 3-continued

MSP Primers

Unmeth-specific

| | | |
|---|---|---|
| fwd: | 5'-TGTGTGTGTTGTGGTGTTGTT-3' | (SEQ ID NO: 20) |
| rev: | 5'-CTTCCACCCACAAAATCCAT-3' | (SEQ ID NO: 21) |

PROX GR 10
Meth-specific

| | | |
|---|---|---|
| fwd: | 5'-GTTCGTTTTTTCGAGGTGTC-3' | (SEQ ID NO: 22) |
| rev: | 5'-AACCAACGCTATCACCCG-3' | (SEQ ID NO: 23) |

Unmeth-specific

| | | |
|---|---|---|
| fwd: | 5'-TTTGTTTTTTTGAGGTGTTG-3' | (SEQ ID NO: 24) |
| rev: | 5'-AAAAACCAACACTATCACCCAC-3' | (SEQ ID NO: 25) |

PROX GR 11
Meth-specific

| | | |
|---|---|---|
| fwd: | 5'-CGCGTGAGGGTGTATACG-3' | (SEQ ID NO: 26) |
| rev: | 5'-CGCAATCTCCAAATTACGAA-3' | (SEQ ID NO: 27) |

Unmeth-specific

| | | |
|---|---|---|
| fwd: | 5'-GGGGTGTGTGAGGGTGTATAT-3' | (SEQ ID NO: 28) |
| rev: | 5'-CCACAATCTCCAAATTACAAA-3' | (SEQ ID NO: 29) |

The primers set forth in Tables 2 and 3 are particularly useful in detecting methylated GR in nipple aspirate, ductal lavage, blood, plasma or serum.

The kit can also include instructions for carrying out methods for diagnosing breast cancer and/or prognosticating outcome of a subject with breast cancer, as well as positive and/or negative controls, to ensure the system is properly functioning and controls (e.g., normal tissue) for assessing the presence, absence, or level of GR promoter methylation and/or level of BRCA1 gene expression, and/or determining whether the breast cancer is ER+ or ER−.

The following nonlimiting examples are provided to further illustrate the present invention.

EXAMPLES

Example 1: 5' RACE

5' Rapid Amplification of cDNA Ends (RACE) of primary total normal breast RNA (Invitrogen, Carlsbad, Calif.) and 184-hTert and MCF-7 RNA was performed using the SMARTER RACE cDNA Amplification Kit (Clontech Laboratories, Mountain View, Calif.) and a gene-specific reverse primer (Turner, et al. (2005) supra) with a BamHI cut site (GR exon $2_{(Det)}$: 5'-GGG GGA TCC CAG TGG ATG CTG AAC TCT TGG-3' (SEQ ID NO:30)). Nested reverse primers were designed in GR exon 2 also containing BamHI cut sites (GR exon 2-2: 5'-GGG GGA TCC CGA CAG CCA GTG AGG GTG AAG ACG-3' (SEQ ID NO:31)) and GR exon 2-1: 5'-GGG GGA TCC GGG TTT TAT AGA AGT CCA TCA CAT CTC C-3'(SEQ ID NO:32)), and a variation of the forward SMARTER II A Oligonucleotide was designed with an XbaI cut site (SMART: 5'-GGG TCT AGA AAG CAG TGG TAT CAA CGC AGA G-3' (SEQ ID NO:33)).

Nested PCR amplification was performed using the following program: 94° C. for 15 minutes followed by 35 cycles: denaturing at 94° C. for 30 seconds, annealing at 68° C. for 30 seconds, elongation at 72° C. for 2 minutes, ending with 4 minutes at 72° C. Amplification products were purified using the QIAQUICK PCR Purification Kit (Qiagen, Hilden, Germany), cloned into a pBS+ vector, and plated. Colonies were selected using IPTG/X-gal color selection and processed using the QIAPREP Spin Miniprep Kit (Qiagen). 5' RACE products were subsequently subjected to sequence analysis (ACGT Inc., Wheeling, Ill.).

Example 2: Homogenization and DNA/RNA Extraction of Breast Clinical Samples

Matched tumor and normal breast clinical tissue samples were obtained from the Ontario Tumor Bank from 59 breast cancer patients. The majority of samples were between 50 and 69 years of age (Table 4) and the predominant hormone receptor subtype was ER+/PR+/Her2− (Table 5). Some patient samples had unknown ER, PR, or Her2 status and are included in the "Other" category.

TABLE 4

| Age | Number of Samples |
|---|---|
| 20-29 | 1 |
| 30-39 | 4 |
| 40-49 | 8 |
| 50-59 | 15 |
| 60-69 | 14 |
| 70-79 | 9 |
| 80-89 | 7 |
| 90-99 | 1 |

TABLE 5

| Hormone Receptor Status | Number of Samples |
|---|---|
| ER+/PR+/Her2+ | 2 |
| ER+/PR+/Her2− | 33 |
| ER−/PR−/Her2+ | 8 |
| ER−/PR−/Her2− | 4 |
| Other (including UNK) | 12 |

All samples were homogenized using a 7 mm×150 mm generator (PRO Scientific, Oxford, Conn.) on setting 5 for 1 minute, or until completely homogenized. DNA and RNA were extracted using the ALLPREP DNA/RNA Mini Kit (Qiagen) reagents and modified protocol. RNA sample quality was assessed by RNA Integrity Number (RIN) obtained using a Bioanalyzer electrophoresis assay (Agilent Technologies, Santa Clara, Calif.). Only RNA samples with RIN above 6 were used for qRT-PCR analysis. DNA samples used for MeDIP-qPCR analysis were run on 0.7% agarose gels to assess DNA quality.

Example 3: qRT-PCR

Synthesis of cDNA and subsequent PCR amplification of RNA was achieved using the SUPERSCRIPT III PLATINUM One-Step Quantitative RT-PCR System (Invitrogen) and TAQMAN Gene Expression Assay probe and primer sets (Applied Biosystems, Carlsbad, Calif.) for NR3C1 and BRCA1 using HPRT1 as an internal control. The qRT-PCR reaction was run in a MASTERCYCLER realplex[4] (Eppendorf, Hamburg, Germany) using the following program: 50° C. for 15 minute, 95° C. for 2 minutes, followed by cycles: denaturing at 95° C. for 15 seconds, annealing at 60° C. for 30 seconds. Quantitation of specific transcript levels was determined using the ΔΔCt Method and analysis of relative gene expression between samples was achieved by normalizing all samples to GR and BRCA1 expression in A00235 normal tissue.

Example 4: MeDIP-qPCR

Genomic DNA obtained from breast cancer patient samples was sheared using a Sonic Dismembrator Model 100 (Fisher Scientific). Methylated DNA immunoprecipitation was performed for 1 μg of sheared DNA using the MeDIP Kit (Active Motif, Carlsbad, Calif.) reagents and protocol. Samples were incubated with 5-methylcytosine (5-meC) antibody overnight and fractionated into flow-through and methylated DNA (MeDNA) fractions, which were then purified. Quantitative PCR (qPCR) was conducted using QUANTITECT SYBR Green PCR Kit (Qiagen) using primers designed for the BRCA1 and GR promoters. BRCA1 promoter primers were F1: 5'-AGG GCG GAA AGA GTG GGG GAT T-3' (SEQ ID NO:34), R1: 5'-CAG TCT GCC CCC GGA TGA CG-3' (SEQ ID NO:35), F2: 5'-ACG TCA TCC GGG GGC AGA CT-3' (SEQ ID NO:36), R2: 5'-CCC GCG CTT TTC CGT TGC C-3' (SEQ ID NO:37), F3: 5'-CAG AGC CCC GAG AGA CGC TTG-3' (SEQ ID NO:38), R3: 5'-GCC GCG CAG TCG CAG TTT TA-3' (SEQ ID NO:39). GR promoter primers were prox GR 2 fwd: 5'-GTC CAA GCC TTC CCG ACG CG-3' (SEQ ID NO:40), rev: 5'-CCC TCG ACT CTG TGC GTT GCT-3' (SEQ ID NO:41), prox GR 3 fwd: 5'-GCA ACG CAC AGA GTC GAG GGC-3' (SEQ ID NO:42), rev: 5'-CGC CCA ATG TGC TCA CAC TCG-3' (SEQ ID NO:43), prox GR 5 fwd: 5'-CCC CGG GCC CAA AGT ACG TAT GCG-3' (SEQ ID NO:44), rev: 5'-GCG GCT GAG CTG CGT GAG TGG-3' (SEQ ID NO:45), prox GR 8 fwd: 5'-CGA GTG TGT GCG CGC CGT-3' (SEQ ID NO:46), rev: 5'-CGG CGT CTC CTT CCA CCC AC-3' (SEQ ID NO:47), prox GR 10 fwd: 5'-CCG CCG CGG GAG CCT ACA AA-3' (SEQ ID NO:48), rev: 5'-ACG AAA ACG GGT GTC GGG CG-3' (SEQ ID NO:49), prox GR 11 fwd: 5'-TCG CCC GAC ACC CGT TTT CG-3' (SEQ ID NO:50), rev: 5'-AAC AGA TAA CGC CGG CCC CG-3' (SEQ ID NO:51). qPCR was performed in a MASTERCYCLER realplex[4] (Eppendorf) using the following program: 94° C. for 15 min followed by 40 cycles: denaturing at 94° C. for 30 seconds, annealing at 60° C. for 30 seconds, elongation at 72° C. for 30 seconds. Cycle threshold (Ct) values for each primer set were obtained for both the flow-through and MeDNA fractions and ΔCt=Ct MeDNA−Ct flow-through was calculated for each sample.

Example 5: Hypomethylation of UACC-3199 Cells

UACC-3199 cells were cultured in RPMI-1640 media containing 10% fetal bovine serum (FBS) and 1× penicillin and streptomycin. Cells were treated with 50 ng/mL 5'-aza-2-deoxycytidine (Sigma, St Louis, Mo.) and 50 ng/mL trichostatin A (Sigma), 50 ng/mL 5'-aza-2-deoxycytidine alone, or vehicle controls for 48 hours. After treatment, cells were cultured in normal media for 48 hours and DNA was harvested using the ALLPREP DNA/RNA Mini Kit (Qiagen) reagents and protocol.

Example 6: Statistical Analysis

Student's T-tests were performed in order to determine statistical significance. Correlative analysis was performed using two-tailed p-value correlation analysis assuming a non-parametric correlation using the Spearman rank-order coefficient.

What is claimed is:

1. A method for detecting methylated glucocorticoid receptor (GR) proximal promoter in a human with breast cancer, said method comprising:
   subjecting a DNA sample from the human to a technique for detecting methylated DNA in a region consisting of nucleotide 180 through 2673 of SEQ ID NO:1;
   determining from the technique a level of methylation in said region; and
   identifying humans with breast cancer having a level of methylation in said region above a control level.

2. The method of claim 1 wherein the DNA sample is isolated from breast tissue, blood, serum, plasma, urine, ductal lavage or nipple aspirate.

3. The method of claim 1 further comprising measuring a level of GR gene expression in the human relative to a standard level.

4. The method of claim 1 wherein the technique is selected from the group consisting of immunoprecipitation of methylated DNA, methylation specific binding protein columns, methylation-sensitive restriction digestion, methylation sensitive PCR, matrix assisted laser desorption/ionization and time-of-flight mass spectrometry, methylation-specific PCR, fluorescence-based real-time PCR, combined bisulfite restriction analysis, nanopore separation, and direct analysis of bisulfite converted DNA.

5. The method of claim 1 wherein methylation in said region consisting of nucleotide 180 through 2673 of SEQ ID NO:1 is detected by amplifying said region with a primer set.

6. The method of claim 5 wherein the primer set amplifies the region between forward primer SEQ ID NO: 40 and reverse primer SEQ ID NO:51.

* * * * *

SEQUENCE LISTING

<160> NUMBER OF SEQ ID NOS: 51

<210> SEQ ID NO 1
<211> LENGTH: 4470
<212> TYPE: DNA
<213> ORGANISM: Homo sapien

<400> SEQUENCE: 1

| | | | | | |
|---|---|---|---|---|---|
| gagcaggatt | aggtggagct | gcggcagccc | ccgcccgtgt | caggagctgg | caagcgatgt | 60 |
| cacctgtggg | ggcgcaaaag | ttacctcccc | aaaccctaaa | cccacacagc | acaacctttc | 120 |
| ccagagtcac | aaaaatcata | atctgtgccg | cacaaggtag | gaggctcggt | cccggcatcg | 180 |
| tccaagcctt | cccgacgcgg | cgagctgggg | aagggagctg | gggcgggggc | ttcccgcacg | 240 |
| ggcacccctc | gccccacggc | cctctccttt | ctcaggacgg | accacgagtt | cccttcccct | 300 |
| tggactgagg | gggaagctcc | taacaggaac | atctgtaggg | agttgaacgc | tggcattttg | 360 |
| aagctgcctg | tattttgttt | tatttgtagg | ggcaggggtc | ctatgaacgt | gatagggtga | 420 |
| gcaacgcaca | gagtcgaggg | cagcaaatgt | caagattcgg | gggtggggcc | tgcaccggga | 480 |
| acttggacgc | gggccctggc | cggggtggaa | gagaggtca | ggagtttcgg | aagggggct | 540 |
| atatttcgcc | agcaacttac | tatttcgcct | gcaacttgct | tttaagcctg | ccgcccctg | 600 |
| ctttccttaa | tcataataat | aaaaaaaaag | tgcaaagaaa | tccagctcgc | tggaggtttt | 660 |
| gcatttggcg | tgcaacttcc | ttcgagtgtg | agcacattgg | gcgggagggg | tgggggttga | 720 |
| acttggcagg | cggcgcctcc | ttctgccgcc | gccgccgcct | cgcagactcg | gggaagaggg | 780 |
| tggggacgg | tcggggcgcg | gggagggtg | ggttctgctt | tgcaacttct | ctcccagtgc | 840 |
| gagagcgcgg | cggcggcagc | tgaagacccg | gccgcccaga | tgatgcggtg | gtgggggacc | 900 |
| tgccggcacg | cgactccccc | ccgggcccaa | agtacgtatg | cgccgacccc | cgctatcccg | 960 |
| tcccttccct | gaagcctccc | cagagggcgt | gtcaggccgc | ccggcccga | gcgcggccga | 1020 |
| gacgctgcgg | caccgtttcc | gtgcaacccc | gtagccccctt | tcgaagtgac | acacttcacg | 1080 |
| caactcggcc | cggcggcggc | ggcgcgggcc | actcacgcag | ctcagccgcg | ggaggcgccc | 1140 |
| cggctcttgt | ggcccgcccg | ctgtcacccg | caggggcact | ggcggcgctt | gccgccaagg | 1200 |
| ggcagagcga | gctcccgagt | gggtctggag | ccgcggagct | gggcgggggc | gggaaggagg | 1260 |
| tagcgagaaa | agaaactgga | gaaactcggt | ggccctctta | acgccgcccc | agagagacca | 1320 |
| ggtcggcccc | cgccgctgcc | gccgccaccc | tttttcctgg | ggagttgggg | gcggggggcg | 1380 |
| aagcgcggcg | caccgggcgg | ggcggccacg | ccaggggacg | cgggcgtgca | ggcgccgtcg | 1440 |
| gggccggggt | ggcggggccc | gcgcggaggg | cgtgggggca | gggaccgcgg | gcgcccctgc | 1500 |
| agttgccaag | cgtcaccaac | aggttgcatc | gttccccgcg | gccgccgcgc | ggcccctcgg | 1560 |
| gcggggagcg | gccggggtg | gagtgggagc | gcgtgtgtgc | gagtgtgtgc | gcgccgtggc | 1620 |
| gccgcctcca | cccgctcccc | gctcggtccc | gctcgctcgc | ccaggccggg | ctgcccttc | 1680 |
| gcgtgtccgc | gctctcttcc | ctccgccgcc | gcctcctcca | ttttgcgagc | tcgtgtctgt | 1740 |
| gacgggagcc | cgagtcaccg | cctgcccgtc | ggggacggat | tctgtgggtg | gaaggagacg | 1800 |
| ccgcagccgg | agcggccgaa | gcagctggga | ccgggacggg | gcacgcgcgc | ccggaagccc | 1860 |
| cgacccgcgg | agcccggcgc | ggggcggagg | gctggcttgt | cagctgggca | atgggagact | 1920 |
| ttcttaaata | ggggctctcc | ccccacccat | ggagaaaggg | gcggctgttt | acttcctttt | 1980 |
| tttagaaaaa | aaaaatatat | ttccctcctg | ctccttctgc | gttcacaagc | taagttgttt | 2040 |
| atctcggctg | cggcgggaac | tgcggacggt | ggcgggcgag | cggctcctct | gccagaggta | 2100 |

```
agaagcgagg cggggagggggg ccggggcgcg ctcgctcccc cgaggtgccg ctgggaccgg    2160
agacaactcg ggggccgccg cgggagccta caaactttta ttagcctcgg ggagtggggg    2220 tgggggggctg gcaagggccg ggcgacggtg acgaaagggc agcgcgcggg tgacagcgct    2280
ggcctcttcc tctccctccg ccggcgtccc ctggccgggc cgaggggggag gaacctgacc    2340 tcggacggcg agcggagccc tgtcgaactg ccgggggctt cgagcctctc attcctcgcg    2400
ggaatcctgg cctcttttct cccctagtg tccctttcc ctccaagggg gtcgcccgac    2460
acccgttttc gtggtgaacg ctaagccgcg tctgaatttt actcgcccga atatttgcac    2520
gccaccccgg cgcgcccgag cgcgagcccg ggctccgggg aggcccccggc ggcgcctggc    2580 ttgaggaggg cgtgcggggc gcgtgagggt gcacacgcgg ggggctgaca gcccgcaact    2640
tggagactgc ggccgggggcc ggcgttatct gttagaagtg ggcgtgtcgg agagagaact    2700
caacaggtct ggacgtactt ctcttttaac ctcgcacttt tttctcttct ccaccccgc    2760 cccgcaaggg cttgctcttt agcgtttgtt gttaattcgc gcctgaggtt tctaagtggc    2820
cccttttaga aaagacccc ctgtaaccgt aatggttttg tgctgcgatt tttacaagtg    2880
ctagtttgac gtttgggggtt gcagacttga taattgcaac cttgtaatac cacttaagac    2940
cctctggcat ggttcattag ggccaattaa tgtggctggg ttatttgcaa cttaaactgg    3000
gggataatgt cgcttgaggg agcgttttcg ttttaggaaa tattgttttg gtttcgggtt    3060
tgaaggcagc tgtcaaaaaa gcggcatgga aattcattgg gctccattcg atacctcgtg    3120
tttagagatc gttatcgcct cagataaacg gggcagagag gtggggagat aagcagttta    3180
ccctcaagat ttgtagtggc aagtccacac ccctctctct accttcatat tcacttttca    3240
gtgagggcca gtgacattta tgctgcctaa cgtcatcgca taggaaaagt tacctttat    3300 tggacgggat ttgactatag tgtcccaaat gcgcttctcc gtcttagccc atctcttaaa    3360
acaccctgat taacgatata ctaacagtct tactctcttg agaataggct gagaattggg    3420
ataggtgaag gtttggatag gtgaaggcag agaaaattat tttgaacatt ttactggata    3480
cagttgtacc tgaatttata tgaatgtgat tttacggttc tgtgtttttc cattttcag    3540 tacttcgata tttgtttgga aaggaaagaa cttagagatg taatagcatt tcatattgag    3600
gatctcaagc aatgtaaaca aatgtagctt aatctagatg ttttttgtgag ttatgataag    3660 ggtcagctat atttaagtta tgtaagctaa caacgtagtg agaaactact acaccttctc    3720
ttctgctctt taaaatctaa atttagttg gcctatataa agtgtatctc atttcatata    3780
tccaaaattt ggaggtaggc acatccagtc agaagtatgg gttaaaaagc ttttcccag    3840 cctgtcggaa gataagcaga tcagcattgt ttattttca agaaaacgt gcatggttca    3900 ccagttggtt gtactcaaag gtttggatgt gtgactagct ggtaggaggg aaatttggaa    3960
gtaattaggg attgagaatt ctagcatagt atttatcaaa tgttatatgt attggttctc    4020
agaaaagcaa acagccgtga ttgaaaagag gtaggaattt taatgatcac acttcctttt    4080
tttgaaatta aatactttga catcaacttg aaccttcaga ataatcagat gtaatgaatt    4140
ataatgtctg tgattaacaa agctacacgt tcagtaatcg gcaggatgaa tagccaagct    4200
tagttcgata cacttttgcc ctcagctgtg caaatggatt gcattgtact tttaaatgtg    4260
gcatgctgaa tgggagcagg ggacatggct ttttattctg gaagatagaa actactcttc    4320
tggtaacaaa gaatttgatt cggagttaac taaaaggttc atttaacaag ctgcctctta    4380
ctaatcggat caggaagata atgtgacttt agagcttatg atgttttccc cccgttttg    4440
``` tttttttgttt tgtagttgat attcactgat                                              4470

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
gctttgcaac ttctctccca g                                                        21

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
ggtcggcgca tacgtacttt                                                          20

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
tatcccgtcc cttccctgaa                                                          20

<210> SEQ ID NO 5
<211> LENGTH: 20
<212> TYPE: DNA
<213> ORGANISM: Artificial sequence
<220> FEATURE:
<223> OTHER INFORMATION: Synthetic

<400> SEQUENCE: 5
tcacttcgaa aggggctacg                                                          20

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
cgtagcccct ttcgaagtga                                                          20

<210> SEQ ID NO 7
<211> LENGTH: 18
<212> TYPE: DNA
<213> ORGANISM: Artificial sequence
<220> FEATURE:
<223> OTHER INFORMATION: Synthetic

<400> SEQUENCE: 7
gctgagctgc gtgagtgg                                                            18

<210> SEQ ID NO 8
<211> LENGTH: 25
<212> TYPE: DNA
<213> ORGANISM: Artificial sequence

```
<220> FEATURE:
<223> OTHER INFORMATION: Synthetic

<400> SEQUENCE: 8
cgcgggagcc tacaaacttt tatta                                              25

<210> SEQ ID NO 9
<211> LENGTH: 18
<212> TYPE: DNA
<213> ORGANISM: Artificial sequence
<220> FEATURE:
<223> OTHER INFORMATION: Synthetic

<400> SEQUENCE: 9 gctgccctttt cgtcaccg                                                     18

<210> SEQ ID NO 10
<211> LENGTH: 19
<212> TYPE: DNA
<213> ORGANISM: Artificial sequence
<220> FEATURE:
<223> OTHER INFORMATION: Synthetic

<400> SEQUENCE: 10
tggcctcttc ctctccctc                                                     19

<210> SEQ ID NO 11
<211> LENGTH: 17
<212> TYPE: DNA
<213> ORGANISM: Artificial sequence
<220> FEATURE:
<223> OTHER INFORMATION: Synthetic

<400> SEQUENCE: 11
gttcgacagg gctccgc                                                       17

<210> SEQ ID NO 12
<211> LENGTH: 19
<212> TYPE: DNA
<213> ORGANISM: Artificial sequence
<220> FEATURE:
<223> OTHER INFORMATION: Synthetic

<400> SEQUENCE: 12
aggaacctga cctcggacg                                                     19

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
cgaggaatga gaggctcgaa                                                    20

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
tagagggcgt gttaggtcgt                                                    20
```

<210> SEQ ID NO 15
<211> LENGTH: 18
<212> TYPE: DNA
<213> ORGANISM: Artificial sequence
<220> FEATURE:
<223> OTHER INFORMATION: Synthetic

<400> SEQUENCE: 15
gccgaaccga attacgta                                                   18

<210> SEQ ID NO 16
<211> LENGTH: 21
<212> TYPE: DNA
<213> ORGANISM: Artificial sequence
<220> FEATURE:
<223> OTHER INFORMATION: Synthetic

<400> SEQUENCE: 16
ttagagggtg tgttaggttg t                                               21

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
ccaccaaacc aaattacata                                                 20

<210> SEQ ID NO 18
<211> LENGTH: 18
<212> TYPE: DNA
<213> ORGANISM: Artificial sequence
<220> FEATURE:
<223> OTHER INFORMATION: Synthetic

<400> SEQUENCE: 18
gtggcgtcgt ttttattc                                                   18

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
aaataaaaaa aacgacgacg                                                 20

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20
tgtgtgtgtt gtggtgttgt t                                               21

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21
cttccaccca caaaatccat                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic

<400> SEQUENCE: 22
gttcgttttt tcgaggtgtc                                               20

<210> SEQ ID NO 23
<211> LENGTH: 18
<212> TYPE: DNA
<213> ORGANISM: Artificial sequence
<220> FEATURE:
<223> OTHER INFORMATION: Synthetic

<400> SEQUENCE: 23
aaccaacgct atcacccg                                                 18

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
tttgtttttt tgaggtgttg                                               20

<210> SEQ ID NO 25
<211> LENGTH: 22
<212> TYPE: DNA
<213> ORGANISM: Artificial sequence
<220> FEATURE:
<223> OTHER INFORMATION: Synthetic

<400> SEQUENCE: 25
aaaaaccaac actatcaccc ac                                            22

<210> SEQ ID NO 26
<211> LENGTH: 18
<212> TYPE: DNA
<213> ORGANISM: Artificial sequence
<220> FEATURE:
<223> OTHER INFORMATION: Synthetic

<400> SEQUENCE: 26
cgcgtgaggg tgtatacg                                                 18

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
cgcaatctcc aaattacgaa                                               20

<210> SEQ ID NO 28

```
<211> LENGTH: 21
<212> TYPE: DNA
<213> ORGANISM: Artificial sequence
<220> FEATURE:
<223> OTHER INFORMATION: Synthetic

<400> SEQUENCE: 28
ggggtgtgtg agggtgtata t                                              21

<210> SEQ ID NO 29
<211> LENGTH: 21
<212> TYPE: DNA
<213> ORGANISM: Artificial sequence
<220> FEATURE:
<223> OTHER INFORMATION: Synthetic

<400> SEQUENCE: 29
ccacaatctc caaattacaa a                                              21

<210> SEQ ID NO 30
<211> LENGTH: 30
<212> TYPE: DNA
<213> ORGANISM: Artificial sequence
<220> FEATURE:
<223> OTHER INFORMATION: Synthetic

<400> SEQUENCE: 30
gggggatccc agtggatgct gaactcttgg                                     30

<210> SEQ ID NO 31
<211> LENGTH: 33
<212> TYPE: DNA
<213> ORGANISM: Artificial sequence
<220> FEATURE:
<223> OTHER INFORMATION: Synthetic

<400> SEQUENCE: 31
gggggatccc gacagccagt gagggtgaag acg                                 33

<210> SEQ ID NO 32
<211> LENGTH: 37
<212> TYPE: DNA
<213> ORGANISM: Artificial sequence
<220> FEATURE:
<223> OTHER INFORMATION: Synthetic

<400> SEQUENCE: 32
ggcggatccg ggttttatag aagtccatca catctcc                             37

<210> SEQ ID NO 33
<211> LENGTH: 31
<212> TYPE: DNA
<213> ORGANISM: Artificial sequence
<220> FEATURE:
<223> OTHER INFORMATION: Synthetic

<400> SEQUENCE: 33
gggtctagaa agcagtggta tcaacgcaga g                                   31

<210> SEQ ID NO 34
<211> LENGTH: 22
<212> TYPE: DNA
<213> ORGANISM: Artificial sequence
<220> FEATURE:
<223> OTHER INFORMATION: Synthetic

<400> SEQUENCE: 34
```

```
agggcggaaa gagtgggga tt                                                    22

<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
cagtctgccc ccggatgacg                                                      20

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
acgtcatccg ggggcagact                                                      20

<210> SEQ ID NO 37
<211> LENGTH: 19
<212> TYPE: DNA
<213> ORGANISM: Artificial sequence
<220> FEATURE:
<223> OTHER INFORMATION: Synthetic

<400> SEQUENCE: 37
cccgcgcttt tccgttgcc                                                       19

<210> SEQ ID NO 38
<211> LENGTH: 21
<212> TYPE: DNA
<213> ORGANISM: Artificial sequence
<220> FEATURE:
<223> OTHER INFORMATION: Synthetic

<400> SEQUENCE: 38
cagagccccg agagacgctt g                                                    21

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
gccgcgcagt cgcagtttta                                                      20

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
gtccaagcct tcccgacgcg                                                      20

<210> SEQ ID NO 41
<211> LENGTH: 21
<212> TYPE: DNA
```

```
<213> ORGANISM: Artificial sequence
<220> FEATURE:
<223> OTHER INFORMATION: Synthetic

<400> SEQUENCE: 41
ccctcgactc tgtgcgttgc t                                                   21

<210> SEQ ID NO 42
<211> LENGTH: 21
<212> TYPE: DNA
<213> ORGANISM: Artificial sequence
<220> FEATURE:
<223> OTHER INFORMATION: Synthetic

<400> SEQUENCE: 42
gcaacgcaca gagtcgaggg c                                                   21

<210> SEQ ID NO 43
<211> LENGTH: 21
<212> TYPE: DNA
<213> ORGANISM: Artificial sequence
<220> FEATURE:
<223> OTHER INFORMATION: Synthetic

<400> SEQUENCE: 43
cgcccaatgt gctcacactc g                                                   21

<210> SEQ ID NO 44
<211> LENGTH: 24
<212> TYPE: DNA
<213> ORGANISM: Artificial sequence
<220> FEATURE:
<223> OTHER INFORMATION: Synthetic

<400> SEQUENCE: 44
ccccgggccc aaagtacgta tgcg                                                24

<210> SEQ ID NO 45
<211> LENGTH: 21
<212> TYPE: DNA
<213> ORGANISM: Artificial sequence
<220> FEATURE:
<223> OTHER INFORMATION: Synthetic

<400> SEQUENCE: 45
gcggctgagc tgcgtgagtg g                                                   21

<210> SEQ ID NO 46
<211> LENGTH: 18
<212> TYPE: DNA
<213> ORGANISM: Artificial sequence
<220> FEATURE:
<223> OTHER INFORMATION: Synthetic

<400> SEQUENCE: 46
cgagtgtgtg cgcgccgt                                                       18

<210> SEQ ID NO 47
<211> LENGTH: 20
<212> TYPE: DNA
<213> ORGANISM: Artificial sequence
<220> FEATURE:
<223> OTHER INFORMATION: Synthetic

<400> SEQUENCE: 47
cggcgtctcc ttccacccac                                                     20
```

```
<210> SEQ ID NO 48
<211> LENGTH: 20
<212> TYPE: DNA
<213> ORGANISM: Artificial sequence
<220> FEATURE:
<223> OTHER INFORMATION: Synthetic

<400> SEQUENCE: 48
ccgccgcggg agcctacaaa                                               20

<210> SEQ ID NO 49
<211> LENGTH: 20
<212> TYPE: DNA
<213> ORGANISM: Artificial sequence
<220> FEATURE:
<223> OTHER INFORMATION: Synthetic

<400> SEQUENCE: 49
acgaaaacgg gtgtcgggcg                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic

<400> SEQUENCE: 50
tcgcccgaca cccgttttcg                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic

<400> SEQUENCE: 51
aacagataac gccggccccg                                               20
```